US010365289B2

(12) United States Patent
Rubio Somoza et al.

(10) Patent No.: US 10,365,289 B2
(45) Date of Patent: Jul. 30, 2019

(54) SENSOR PEPTIDE AND METHODS OF USE THEREOF TO IDENTIFY SUBSTANCES THAT MODULATE GIBBERELLIC ACID ACTION

(71) Applicant: Max-Planck-Gesellschaft zur Forderung der Wissenschaften e.V., Munich (DE)

(72) Inventors: Ignacio Rubio Somoza, Santiago de Compostela (ES); Michael Sauer, Reutlingen (DE); Detlef Weigel, Tübingen (DE)

(73) Assignee: Max-Planck-Gesellschaft zur Forderung der Wissenschaften e.V., Munich (DE)

( * ) Notice: Subject to any disclaimer, the term of this patent is extended or adjusted under 35 U.S.C. 154(b) by 228 days.

(21) Appl. No.: 15/117,817

(22) PCT Filed: Feb. 16, 2015

(86) PCT No.: PCT/EP2015/053208
§ 371 (c)(1),
(2) Date: Aug. 10, 2016

(87) PCT Pub. No.: WO2015/121468
PCT Pub. Date: Aug. 20, 2015

(65) Prior Publication Data

US 2017/0052201 A1 Feb. 23, 2017

(30) Foreign Application Priority Data

Feb. 15, 2014 (EP) .................................... 14155302

(51) Int. Cl.

| | |
|---|---|
| ***C12R 1/865*** | (2006.01) |
| ***G01N 33/50*** | (2006.01) |
| ***G01N 33/58*** | (2006.01) |
| ***G01N 33/74*** | (2006.01) |
| ***C07K 14/415*** | (2006.01) |
| ***G01N 33/566*** | (2006.01) |

(52) U.S. Cl.
CPC ........... *G01N 33/74* (2013.01); *C07K 14/415* (2013.01); *C12R 1/865* (2013.01); *G01N 33/5097* (2013.01); *G01N 33/566* (2013.01); *G01N 33/581* (2013.01); *G01N 2333/39* (2013.01); *G01N 2333/415* (2013.01); *G01N 2500/02* (2013.01); *G01N 2500/04* (2013.01); *G01N 2500/10* (2013.01)

(58) Field of Classification Search
CPC .. G01N 33/5097; G01N 33/74; G01N 33/566; G01N 33/581; G01N 2500/10; G01N 2333/39; G01N 2333/415; G01N 2500/02; G01N 2500/04; C12R 1/865; C07K 14/415
See application file for complete search history.

(56) References Cited

PUBLICATIONS

International Search Report for International Patent Application No. PCT/EP2015/053208 dated Apr. 30, 2015, 4 pages.
Written Opinion for International Patent Application No. PCT/EP2015/053208 dated Apr. 30, 2015, 7 pages.
Hao, et al. "Computational Gibberellin-Binding Channel Discovery Unraveling the Unexpected Perception Mechanism of Hormone Signal by Gibberlin Receptor", J Comput Chem (2013) 34: 2055-2064.
Hall, "BioEdit: a user-friendly biological sequence alignment editor and analysis program for Windows 95/98/NT", Nucleic Acids Symp Ser (1999) 41: 95-98.
Sun, et al. "Cloning the Arabidopsis GA1 Locus by Genomic Subtraction", Plant Cell (1992) 4: 119-128.
Hu, et al. "Potential Sites of Bioactive Gibberellin Production during Reproductive Growth in Arabidopsis", Plant Cell (2008) 20: 320-336.
Blazquez, et al. "Leafy expression and flower initiation in Arabidopsis", Development (1997) 124: 3835-3844.

*Primary Examiner* — Robert S Landsman
(74) *Attorney, Agent, or Firm* — Amin, Turocy & Watson LLP

(57) ABSTRACT

The present invention relates to methods of identifying substances that modulate GA action through targeting its receptor or acting as a GA functional analog, sensor peptides especially designed for that methods as well as a strain of the species *Saccharomyces cerevisiae* expressing such a sensor peptide.

14 Claims, 11 Drawing Sheets

Specification includes a Sequence Listing.

Mock    100µM $GA_3$

SEQUENCE LISTING

```
<160> NUMBER OF SEQ ID NOS: 26

<210> SEQ ID NO 1
<211> LENGTH: 939
<212> TYPE: PRT
<213> ORGANISM: Photinus pyralis

<400> SEQUENCE: 1

Met Ser Gly Tyr Val Asn Asn Pro Glu Ala Thr Asn Ala Leu Ile Asp
1               5                   10                  15

Lys Asp Gly Trp Leu His Ser Gly Asp Ile Ala Tyr Trp Asp Glu Asp
            20                  25                  30

Glu His Phe Phe Ile Val Asp Arg Leu Lys Ser Leu Ile Lys Tyr Lys
        35                  40                  45

Gly Tyr Gln Val Ala Pro Ala Glu Leu Glu Ser Ile Leu Leu Gln His
    50                  55                  60

Pro Asn Ile Phe Asp Ala Gly Val Ala Gly Leu Pro Asp Asp Asp Ala
65                  70                  75                  80

Gly Glu Leu Pro Ala Ala Val Val Val Leu Glu His Gly Lys Thr Met
                85                  90                  95

Thr Glu Lys Glu Ile Val Asp Tyr Val Ala Ser Gln Val Thr Thr Ala
            100                 105                 110

Lys Lys Leu Arg Gly Gly Val Val Phe Val Asp Glu Val Pro Lys Gly
        115                 120                 125

Leu Thr Gly Lys Leu Asp Ala Arg Lys Ile Arg Glu Ile Leu Ile Lys
    130                 135                 140

Ala Lys Lys Gly Gly Lys Ile Ala Val Gly Gly Gly Gly Gly Gly Gly
145                 150                 155                 160

Ala Gly Gly Asn Glu Val Asn Leu Asn Glu Cys Lys Arg Ile Val Pro
                165                 170                 175

Leu Asn Thr Trp Val Leu Ile Ser Asn Phe Lys Leu Ala Tyr Lys Val
```

-continued

```
            180                 185                 190

Leu Arg Arg Pro Asp Gly Ser Phe Asn Arg Asp Leu Ala Glu Phe Leu
        195                 200                 205

Asp Arg Lys Val Pro Ala Asn Ser Phe Pro Leu Asp Gly Val Phe Ser
    210                 215                 220

Phe Asp His Val Asp Ser Thr Thr Asn Leu Leu Thr Arg Ile Tyr Gln
225                 230                 235                 240

Pro Ala Ser Leu Leu His Gln Thr Arg His Gly Thr Leu Glu Leu Thr
                245                 250                 255

Lys Pro Leu Ser Thr Thr Glu Ile Val Pro Val Leu Ile Phe Phe His
            260                 265                 270

Gly Gly Ser Phe Thr His Ser Ser Ala Asn Ser Ala Ile Tyr Asp Thr
        275                 280                 285

Phe Cys Arg Arg Leu Val Thr Ile Cys Gly Val Val Val Ser Val
    290                 295                 300

Asp Tyr Arg Arg Ser Pro Glu His Arg Tyr Pro Cys Ala Tyr Asp Asp
305                 310                 315                 320

Gly Trp Asn Ala Leu Asn Trp Val Lys Ser Arg Val Trp Leu Gln Ser
                325                 330                 335

Gly Lys Asp Ser Asn Val Tyr Val Tyr Leu Ala Gly Asp Ser Ser Gly
            340                 345                 350

Gly Asn Ile Ala His Asn Val Ala Val Arg Ala Thr Asn Glu Gly Val
        355                 360                 365

Lys Val Leu Gly Asn Ile Leu Leu His Pro Met Phe Gly Gly Gln Glu
    370                 375                 380

Arg Thr Gln Ser Glu Lys Thr Leu Asp Gly Lys Tyr Phe Val Thr Ile
385                 390                 395                 400

Gln Asp Arg Asp Trp Tyr Trp Arg Ala Tyr Leu Pro Glu Gly Glu Asp
                405                 410                 415

Arg Asp His Pro Ala Cys Asn Pro Phe Gly Pro Arg Gly Gln Ser Leu
            420                 425                 430

Lys Gly Val Asn Phe Pro Lys Ser Leu Val Val Val Ala Gly Leu Asp
        435                 440                 445

Leu Val Gln Asp Trp Gln Leu Ala Tyr Val Asp Gly Leu Lys Lys Thr
    450                 455                 460

Gly Leu Glu Val Asn Leu Leu Tyr Leu Lys Gln Ala Thr Ile Gly Phe
465                 470                 475                 480

Tyr Phe Leu Pro Asn Asn Asp His Phe His Cys Leu Met Glu Glu Leu
                485                 490                 495

Asn Lys Phe Val His Ser Ile Glu Asp Ser Gln Ser Lys Ser Ser Pro
            500                 505                 510

Val Leu Leu Thr Pro Gly Gly Gly Gly Gly Gly Gly Glu Asp Ala Lys
        515                 520                 525

Asn Ile Lys Lys Gly Pro Ala Pro Phe Tyr Pro Leu Glu Asp Gly Thr
    530                 535                 540

Ala Gly Glu Gln Leu His Lys Ala Met Lys Arg Tyr Ala Leu Val Pro
545                 550                 555                 560

Gly Thr Ile Ala Phe Thr Asp Ala His Ile Glu Val Asp Ile Thr Tyr
                565                 570                 575

Ala Glu Tyr Phe Glu Met Ser Val Arg Leu Ala Glu Ala Met Lys Arg
            580                 585                 590

Tyr Gly Leu Asn Thr Asn His Arg Ile Val Val Cys Ser Glu Asn Ser
        595                 600                 605
```

Leu Gln Phe Phe Met Pro Val Leu Gly Ala Leu Phe Ile Gly Val Ala
    610                 615                 620

Val Ala Pro Ala Asn Asp Ile Tyr Asn Glu Arg Glu Leu Leu Asn Ser
625                 630                 635                 640

Met Gly Ile Ser Gln Pro Thr Val Val Phe Val Ser Lys Lys Gly Leu
                645                 650                 655

Gln Lys Ile Leu Asn Val Gln Lys Lys Leu Pro Ile Ile Gln Lys Ile
            660                 665                 670

Ile Ile Met Asp Ser Lys Thr Asp Tyr Gln Gly Phe Gln Ser Met Tyr
        675                 680                 685

Thr Phe Val Thr Ser His Leu Pro Pro Gly Phe Asn Glu Tyr Asp Phe
    690                 695                 700

Val Pro Glu Ser Phe Asp Arg Asp Lys Thr Ile Ala Leu Ile Met Asn
705                 710                 715                 720

Ser Ser Gly Ser Thr Gly Leu Pro Lys Gly Val Ala Leu Pro His Arg
                725                 730                 735

Thr Ala Cys Val Arg Phe Ser His Ala Arg Asp Pro Ile Phe Gly Asn
            740                 745                 750

Gln Ile Ile Pro Asp Thr Ala Ile Leu Ser Val Val Pro Phe His His
        755                 760                 765

Gly Phe Gly Met Phe Thr Thr Leu Gly Tyr Leu Ile Cys Gly Phe Arg
    770                 775                 780

Val Val Leu Met Tyr Arg Phe Glu Glu Glu Leu Phe Leu Arg Ser Leu
785                 790                 795                 800

Gln Asp Tyr Lys Ile Gln Ser Ala Leu Leu Val Pro Thr Leu Phe Ser
                805                 810                 815

Phe Phe Ala Lys Ser Thr Leu Ile Asp Lys Tyr Asp Leu Ser Asn Leu
            820                 825                 830

His Glu Ile Ala Ser Gly Gly Ala Pro Leu Ser Lys Glu Val Gly Glu
        835                 840                 845

Ala Val Ala Lys Arg Phe His Leu Pro Gly Ile Arg Gln Gly Tyr Gly
    850                 855                 860

Leu Thr Glu Thr Thr Ser Ala Ile Leu Ile Thr Pro Glu Gly Asp Asp
865                 870                 875                 880

Lys Pro Gly Ala Val Gly Lys Val Val Pro Phe Phe Glu Ala Lys Val
                885                 890                 895

Val Asp Leu Asp Thr Gly Lys Thr Leu Gly Val Asn Gln Arg Gly Glu
            900                 905                 910

Leu Cys Val Arg Gly Pro Met Ile Met Ser Gly Tyr Val Asn Asn Pro
        915                 920                 925

Glu Ala Thr Asn Ala Leu Ile Asp Lys Asp Gly
    930                 935

<210> SEQ ID NO 2
<211> LENGTH: 1179
<212> TYPE: PRT
<213> ORGANISM: Artificial Sequence
<220> FEATURE:
<223> OTHER INFORMATION: GID1B sensor peptide

<400> SEQUENCE: 2

Met Ser Gly Tyr Val Asn Asn Pro Glu Ala Thr Asn Ala Leu Ile Asp
1               5                   10                  15

Lys Asp Gly Trp Leu His Ser Gly Asp Ile Ala Tyr Trp Asp Glu Asp
            20                  25                  30

-continued

```
Glu His Phe Phe Ile Val Asp Arg Leu Lys Ser Leu Ile Lys Tyr Lys
        35                  40                  45

Gly Tyr Gln Val Ala Pro Ala Glu Leu Glu Ser Ile Leu Leu Gln His
    50                  55                  60

Pro Asn Ile Phe Asp Ala Gly Val Ala Gly Leu Pro Asp Asp Asp Ala
65                  70                  75                  80

Gly Glu Leu Pro Ala Ala Val Val Val Leu Glu His Gly Lys Thr Met
                85                  90                  95

Thr Glu Lys Glu Ile Val Asp Tyr Val Ala Ser Gln Val Thr Thr Ala
            100                 105                 110

Lys Lys Leu Arg Gly Gly Val Val Phe Val Asp Glu Val Pro Lys Gly
        115                 120                 125

Leu Thr Gly Lys Leu Asp Ala Arg Lys Ile Arg Glu Ile Leu Ile Lys
    130                 135                 140

Ala Lys Lys Gly Gly Lys Ile Ala Val Gly Gly Gly Gly Gly Gly Gly
145                 150                 155                 160

Ala Gly Gly Asn Glu Val Asn Leu Asn Glu Cys Lys Arg Ile Val Pro
                165                 170                 175

Leu Asn Thr Trp Val Leu Ile Ser Asn Phe Lys Leu Ala Tyr Lys Val
            180                 185                 190

Leu Arg Arg Pro Asp Gly Ser Phe Asn Arg Asp Leu Ala Glu Phe Leu
        195                 200                 205

Asp Arg Lys Val Pro Ala Asn Ser Phe Pro Leu Asp Gly Val Phe Ser
    210                 215                 220

Phe Asp His Val Asp Ser Thr Thr Asn Leu Leu Thr Arg Ile Tyr Gln
225                 230                 235                 240

Met Ser Gly Tyr Val Asn Asn Pro Glu Ala Thr Asn Ala Leu Ile Asp
                245                 250                 255

Lys Asp Gly Trp Leu His Ser Gly Asp Ile Ala Tyr Trp Asp Glu Asp
            260                 265                 270

Glu His Phe Phe Ile Val Asp Arg Leu Lys Ser Leu Ile Lys Tyr Lys
        275                 280                 285

Gly Tyr Gln Val Ala Pro Ala Glu Leu Glu Ser Ile Leu Leu Gln His
    290                 295                 300

Pro Asn Ile Phe Asp Ala Gly Val Ala Gly Leu Pro Asp Asp Asp Ala
305                 310                 315                 320

Gly Glu Leu Pro Ala Ala Val Val Val Leu Glu His Gly Lys Thr Met
                325                 330                 335

Thr Glu Lys Glu Ile Val Asp Tyr Val Ala Ser Gln Val Thr Thr Ala
            340                 345                 350

Lys Lys Leu Arg Gly Gly Val Val Phe Val Asp Glu Val Pro Lys Gly
        355                 360                 365

Leu Thr Gly Lys Leu Asp Ala Arg Lys Ile Arg Glu Ile Leu Ile Lys
    370                 375                 380

Ala Lys Lys Gly Gly Lys Ile Ala Val Gly Gly Gly Gly Gly Gly Gly
385                 390                 395                 400

Ala Gly Gly Asn Glu Val Asn Leu Asn Glu Cys Lys Arg Ile Val Pro
                405                 410                 415

Leu Asn Thr Trp Val Leu Ile Ser Asn Phe Lys Leu Ala Tyr Lys Val
            420                 425                 430

Leu Arg Arg Pro Asp Gly Ser Phe Asn Arg Asp Leu Ala Glu Phe Leu
        435                 440                 445
```

```
Asp Arg Lys Val Pro Ala Asn Ser Phe Pro Leu Asp Gly Val Phe Ser
    450                 455                 460

Phe Asp His Val Asp Ser Thr Thr Asn Leu Leu Thr Arg Ile Tyr Gln
465                 470                 475                 480

Pro Ala Ser Leu Leu His Gln Thr Arg His Gly Thr Leu Glu Leu Thr
                485                 490                 495

Lys Pro Leu Ser Thr Thr Glu Ile Val Pro Val Leu Ile Phe Phe His
            500                 505                 510

Gly Gly Ser Phe Thr His Ser Ser Ala Asn Ser Ala Ile Tyr Asp Thr
        515                 520                 525

Phe Cys Arg Arg Leu Val Thr Ile Cys Gly Val Val Val Val Ser Val
    530                 535                 540

Asp Tyr Arg Arg Ser Pro Glu His Arg Tyr Pro Cys Ala Tyr Asp Asp
545                 550                 555                 560

Gly Trp Asn Ala Leu Asn Trp Val Lys Ser Arg Val Trp Leu Gln Ser
                565                 570                 575

Gly Lys Asp Ser Asn Val Tyr Val Tyr Leu Ala Gly Asp Ser Ser Gly
            580                 585                 590

Gly Asn Ile Ala His Asn Val Ala Val Arg Ala Thr Asn Glu Gly Val
        595                 600                 605

Lys Val Leu Gly Asn Ile Leu Leu His Pro Met Phe Gly Gly Gln Glu
    610                 615                 620

Arg Thr Gln Ser Glu Lys Thr Leu Asp Gly Lys Tyr Phe Val Thr Ile
625                 630                 635                 640

Gln Asp Arg Asp Trp Tyr Trp Arg Ala Tyr Leu Pro Glu Gly Glu Asp
                645                 650                 655

Arg Asp His Pro Ala Cys Asn Pro Phe Gly Pro Arg Gly Gln Ser Leu
            660                 665                 670

Lys Gly Val Asn Phe Pro Lys Ser Leu Val Val Val Ala Gly Leu Asp
        675                 680                 685

Leu Val Gln Asp Trp Gln Leu Ala Tyr Val Asp Gly Leu Lys Lys Thr
    690                 695                 700

Gly Leu Glu Val Asn Leu Leu Tyr Leu Lys Gln Ala Thr Ile Gly Phe
705                 710                 715                 720

Tyr Phe Leu Pro Asn Asn Asp His Phe His Cys Leu Met Glu Glu Leu
                725                 730                 735

Asn Lys Phe Val His Ser Ile Glu Asp Ser Gln Ser Lys Ser Ser Pro
            740                 745                 750

Val Leu Leu Thr Pro Gly Gly Gly Gly Gly Gly Gly Glu Asp Ala Lys
        755                 760                 765

Asn Ile Lys Lys Gly Pro Ala Pro Phe Tyr Pro Leu Glu Asp Gly Thr
    770                 775                 780

Ala Gly Glu Gln Leu His Lys Ala Met Lys Arg Tyr Ala Leu Val Pro
785                 790                 795                 800

Gly Thr Ile Ala Phe Thr Asp Ala His Ile Glu Val Asp Ile Thr Tyr
                805                 810                 815

Ala Glu Tyr Phe Glu Met Ser Val Arg Leu Ala Glu Ala Met Lys Arg
            820                 825                 830

Tyr Gly Leu Asn Thr Asn His Arg Ile Val Val Cys Ser Glu Asn Ser
        835                 840                 845

Leu Gln Phe Phe Met Pro Val Leu Gly Ala Leu Phe Ile Gly Val Ala
    850                 855                 860

Val Ala Pro Ala Asn Asp Ile Tyr Asn Glu Arg Glu Leu Leu Asn Ser
```

-continued 865 870 875 880

Met Gly Ile Ser Gln Pro Thr Val Val Phe Val Ser Lys Lys Gly Leu
885 890 895

Gln Lys Ile Leu Asn Val Gln Lys Lys Leu Pro Ile Ile Gln Lys Ile
900 905 910

Ile Ile Met Asp Ser Lys Thr Asp Tyr Gln Gly Phe Gln Ser Met Tyr
915 920 925

Thr Phe Val Thr Ser His Leu Pro Pro Gly Phe Asn Glu Tyr Asp Phe
930 935 940

Val Pro Glu Ser Phe Asp Arg Asp Lys Thr Ile Ala Leu Ile Met Asn
945 950 955 960

Ser Ser Gly Ser Thr Gly Leu Pro Lys Gly Val Ala Leu Pro His Arg
965 970 975

Thr Ala Cys Val Arg Phe Ser His Ala Arg Asp Pro Ile Phe Gly Asn
980 985 990

Gln Ile Ile Pro Asp Thr Ala Ile Leu Ser Val Val Pro Phe His His
995 1000 1005

Gly Phe Gly Met Phe Thr Thr Leu Gly Tyr Leu Ile Cys Gly Phe
1010 1015 1020

Arg Val Val Leu Met Tyr Arg Phe Glu Glu Glu Leu Phe Leu Arg
1025 1030 1035

Ser Leu Gln Asp Tyr Lys Ile Gln Ser Ala Leu Leu Val Pro Thr
1040 1045 1050

Leu Phe Ser Phe Phe Ala Lys Ser Thr Leu Ile Asp Lys Tyr Asp
1055 1060 1065

Leu Ser Asn Leu His Glu Ile Ala Ser Gly Gly Ala Pro Leu Ser
1070 1075 1080

Lys Glu Val Gly Glu Ala Val Ala Lys Arg Phe His Leu Pro Gly
1085 1090 1095

Ile Arg Gln Gly Tyr Gly Leu Thr Glu Thr Thr Ser Ala Ile Leu
1100 1105 1110

Ile Thr Pro Glu Gly Asp Asp Lys Pro Gly Ala Val Gly Lys Val
1115 1120 1125

Val Pro Phe Phe Glu Ala Lys Val Val Asp Leu Asp Thr Gly Lys
1130 1135 1140

Thr Leu Gly Val Asn Gln Arg Gly Glu Leu Cys Val Arg Gly Pro
1145 1150 1155

Met Ile Met Ser Gly Tyr Val Asn Asn Pro Glu Ala Thr Asn Ala
1160 1165 1170

Leu Ile Asp Lys Asp Gly
1175

<210> SEQ ID NO 3
<211> LENGTH: 2820
<212> TYPE: DNA
<213> ORGANISM: Artificial Sequence
<220> FEATURE:
<223> OTHER INFORMATION: GID1B sensor nucleotide sequence

<400> SEQUENCE: 3
atgtccggtt atgtaaacaa tccggaagcg accaacgcct tgattgacaa ggatggatgg 60
ctacattctg gagacatagc ttactgggac gaagacgaac acttcttcat cgttgaccgc 120
ctgaagtctc tgattaagta caaaggctat caggtggctc ccgctgaatt ggaatccatc 180
ttgctccaac accccaacat cttcgacgca ggtgtcgcag gtcttcccga cgatgacgcc 240

```
ggtgaacttc ccgccgccgt tgttgttttg gagcacggaa agacgatgac ggaaaaagag    300
atcgtggatt acgtcgccag tcaagtaaca accgcgaaaa agttgcgcgg aggagttgtg    360
tttgtggacg aagtaccgaa aggtcttacc ggaaaactcg acgcaagaaa aatcagagag    420
atcctcataa aggccaagaa gggcggaaag atcgccgtgg gtggcggggg tggcggagga    480
gctggtggta acgaagtcaa ccttaacgaa tgcaagagaa ttgtcccact caacacatgg    540
gtcctcattt ccaatttcaa gcttgcttac aaagtcctcc gtcgccctga cggttctttc    600
aaccgcgacc tcgccgagtt ccttgaccgt aaagttcccg ccaactcttt ccccctcgac    660
ggcgttttct ccttcgacca cgtcgactca acaactaacc ttctcaccag aatctaccaa    720
cctgcgtctc tccttcatca gacccgtcac ggaaccctcg agctaaccaa acctctcagt    780
actacagaga tcgtccctgt tctcattttc ttccatggag gcagcttcac tcattcctcc    840
gccaatagtg ctatctacga cactttctgc cgacgccttg tcaccatttg cggtgttgtt    900
gttgtctctg ttgattaccg gagatcccct gagcatcgct acccttgtgc ttacgacgat    960
ggatggaacg ctctcaactg ggtcaagtcc agagtctggc ttcagagtgg taaagactcc   1020
aatgtttatg tttatttggc tggagatagc tctggaggca acattgctca caatgtcgct   1080
gtcagagcta ccaatgaagg agtcaaagtg ttggggaaca ttcttcttca tccaatgttt   1140
ggtggacagg agaggactca gtctgagaag acccttgatg gcaaatactt tgtgactata   1200
caagatcgag attggtattg gagggcttat ctaccggaag gtgaagatag agatcatcca   1260
gcatgtaatc cctttggccc gagaggtcaa agccttaaag gagtcaactt tccaaagagt   1320
cttgttgttg tcgctggttt agatcttgtt caagattggc aattagccta tgtggatggg   1380
cttaagaaga ctggtcttga agtcaatctt ttgtatttga aacaagctac cattggcttt   1440
tacttcttgc ctaacaatga tcactttcat tgtcttatgg aagagttgaa taagtttgtg   1500
cactccatag aggattctca aagcaagtca agtcctgtgc ttcttactcc tggtggaggc   1560
ggaggcggag gcgaagacgc caaaaacata aagaaaggcc cggcgccatt ctatccgctg   1620
gaagatggaa ccgctggaga gcaactgcat aaggctatga agagatacgc cctggttcct   1680
ggaacaattg cttttacaga tgcacatatc gaggtggaca tcacttacgc tgagtacttc   1740
gaaatgtccg ttcggttggc agaagctatg aaacgatatg ggctgaatac aaatcacaga   1800
atcgtcgtat gcagtgaaaa ctctcttcaa ttctttatgc cggtgttggg cgcgttattt   1860
atcggagttg cagttgcgcc cgcgaacgac atttataatg aacgtgaatt gctcaacagt   1920
atgggcattt cgcagcctac cgtggtgttc gtttccaaaa aggggttgca aaaaattttg   1980
aacgtgcaaa aaaagctccc aatcatccaa aaaattatta tcatggattc taaaacggat   2040
taccagggat ttcagtcgat gtacacgttc gtcacatctc atctacctcc cggttttaat   2100
gaatacgatt ttgtgccaga gtccttcgat agggacaaga caattgcact gatcatgaac   2160
tcctctggat ctactggtct gcctaaaggt gtcgctctgc ctcatagaac tgcctgcgtg   2220
agattctcgc atgccagaga tcctattttt ggcaatcaaa tcattccgga tactgcgatt   2280
ttaagtgttg ttccattcca tcacggtttt ggaatgttta ctacactcgg atatttgata   2340
tgtggatttc gagtcgtctt aatgtataga tttgaagaag agctgtttct gaggagcctt   2400
caggattaca agattcaaag tgcgctgctg gtgccaaccc tattctcctt cttcgccaaa   2460
agcactctga ttgacaaata cgatttatct aatttacacg aaattgcttc tggtggcgct   2520
cccctctcta aggaagtcgg ggaagcggtt gccaagaggt tccatctgcc aggtatcagg   2580
```

-continued

```
caaggatatg ggctcactga gactacatca gctattctga ttacacccga gggggatgat   2640

aaaccgggcg cggtcggtaa agttgttcca ttttttgaag cgaaggttgt ggatctggat   2700

accgggaaaa cgctgggcgt taatcaaaga ggcgaactgt gtgtgagagg tcctatgatt   2760

atgtccggtt atgtaaacaa tccggaagcg accaacgcct tgattgacaa ggatggataa   2820


<210> SEQ ID NO 4
<211> LENGTH: 21
<212> TYPE: DNA
<213> ORGANISM: Artificial Sequence
<220> FEATURE:
<223> OTHER INFORMATION: Primer for GID1b cDNA amplification

<400> SEQUENCE: 4

atggctggtg gtaacgaagt c                                               21


<210> SEQ ID NO 5
<211> LENGTH: 20
<212> TYPE: DNA
<213> ORGANISM: Artificial Sequence
<220> FEATURE:
<223> OTHER INFORMATION: Primer for GID1b cDNA amplification

<400> SEQUENCE: 5

ctaaggagta agaagcacag                                                 20


<210> SEQ ID NO 6
<211> LENGTH: 23
<212> TYPE: DNA
<213> ORGANISM: Artificial Sequence
<220> FEATURE:
<223> OTHER INFORMATION: Primer for amplification of C-terminal domain
      of firefly luciferase

<400> SEQUENCE: 6

atgtccggtt atgtaaacaa tcc                                             23


<210> SEQ ID NO 7
<211> LENGTH: 53
<212> TYPE: DNA
<213> ORGANISM: Artificial Sequence
<220> FEATURE:
<223> OTHER INFORMATION: Primer for amplification of C-terminal domain
      of firefly luciferase with linker

<400> SEQUENCE: 7

gacttcgtta ccaccagctc ctccgccacc cccgccaccc acggcgatct ttc            53


<210> SEQ ID NO 8
<211> LENGTH: 26
<212> TYPE: DNA
<213> ORGANISM: Artificial Sequence
<220> FEATURE:
<223> OTHER INFORMATION: Primer for addition of linker to GID1b cDNA

<400> SEQUENCE: 8

gcggaggagc tggtggtaac gaagtc                                          26


<210> SEQ ID NO 9
<211> LENGTH: 26
<212> TYPE: DNA
<213> ORGANISM: Artificial Sequence
<220> FEATURE:
<223> OTHER INFORMATION: Primer for addition of  linker to GID1b cDNA

<400> SEQUENCE: 9
```

gcctccacca ggagtaagaa gcacag 26

<210> SEQ ID NO 10
<211> LENGTH: 59
<212> TYPE: DNA
<213> ORGANISM: Artificial Sequence
<220> FEATURE:
<223> OTHER INFORMATION: Primer for Addition of linker to N-terminal domain of firefly luciferase

<400> SEQUENCE: 10
ctgtgcttct tactcctggt ggaggcggag gcggaggcga agacgccaaa aacataaag 59

<210> SEQ ID NO 11
<211> LENGTH: 19
<212> TYPE: DNA
<213> ORGANISM: Artificial Sequence
<220> FEATURE:
<223> OTHER INFORMATION: Primer for amplification of N-terminal domain of firefly luciferase

<400> SEQUENCE: 11
ttatccatcc ttgtcaatc 19

<210> SEQ ID NO 12
<211> LENGTH: 2778
<212> TYPE: DNA
<213> ORGANISM: Artificial
<220> FEATURE:
<223> OTHER INFORMATION: GID1C-sensor nucleotide sequence

<400> SEQUENCE: 12
atgtccggtt atgtaaacaa tccggaagcg accaacgcct tgattgacaa ggatggatgg 60
ctacattctg gagacatagc ttactgggac gaagacgaac acttcttcat cgttgaccgc 120
ctgaagtctc tgattaagta caaaggctat caggtggctc ccgctgaatt ggaatccatc 180
ttgctccaac accccaacat cttcgacgca ggtgtcgcag gtcttcccga cgatgacgcc 240
ggtgaacttc ccgccgccgt tgttgttttg gagcacggaa agacgatgac ggaaaaagag 300
atcgtggatt acgtcgccag tcaagtaaca accgcgaaaa agttgcgcgg aggagttgtg 360
tttgtggacg aagtaccgaa aggtcttacc ggaaaactcg acgcaagaaa aatcagagag 420
atcctcataa aggccaagaa gggcggaaag atcgccgtgg gtggcggggg tggcggagga 480
gctggaagtg aagaagttaa tcttattgag agcaagacag tggttcctct caatacatgg 540
gttctaatat ccaactttaa gctagcttac aatctcctgc gtcgccctga cggaactttt 600
aaccgtcatc tcgcagagtt tctagaccgg aaagtccctg caaatgccaa ccctgttaat 660
ggggtcttct cttttgatgt gatcatcgat cgccaaacta atttgcttag cagagtttac 720
agaccagctg atgctggcac ttcaccaagt attactgatc tacagaatcc tgttgatggt 780
gaaatagtgc ctgttattgt cttctttcat ggtggaagct ttgcacattc ttctgcaaac 840
agtgctattt atgatactct ttgtcgtagg cttgttggtt tgtgtggtgc tgttgttgtc 900
tctgtgaatt atcgtcgtgc accagagaat cgataccctt gtgcttatga tgatggatgg 960
gctgttttga aatgggtcaa ctcgagttct tggcttagaa gcaagaaaga ctcaaaggtt 1020
cgtattttct tggcgggtga tagctctggg ggtaacattg tgcataatgt cgcggtaaga 1080
gcggttgagt caaggatcga tgttttgggg aacattttgc ttaaccctat gtttggaggg 1140
accgaaagaa cggaatctga gaaacgtttg gatgggaagt actttgttac ggttagagac 1200

-continued

```
cgagattggt attggagagc gtttcttcct gagggtgaag acagagagca tccagcgtgt   1260

agcccgtttg gcccgagaag caagagtcta gaagggttga gtttccccaa gagtcttgtc   1320

gttgtagcgg gtttagattt gattcaagat tggcaattga agtacgcgga agggctcaag   1380

aaagcgggtc aagaggtgaa gcttctttac ttggagcaag ccactattgg cttctactta   1440

ttgcctaaca acaatcactt ccataccgtt atggatgaga tagctgcatt tgtaaacgca   1500

gaatgccaag gtggaggcgg aggcggaggc gaagacgcca aaaacataaa gaaaggcccg   1560

gcgccattct atccgctgga agatggaacc gctggagagc aactgcataa ggctatgaag   1620

agatacgccc tggttcctgg aacaattgct tttacagatg cacatatcga ggtggacatc   1680

acttacgctg agtacttcga aatgtccgtt cggttggcag aagctatgaa acgatatggg   1740

ctgaatacaa atcacagaat cgtcgtatgc agtgaaaact ctcttcaatt ctttatgccg   1800

gtgttgggcg cgttatttat cggagttgca gttgcgcccg cgaacgacat ttataatgaa   1860

cgtgaattgc tcaacagtat gggcatttcg cagcctaccg tggtgttcgt ttccaaaaag   1920

gggttgcaaa aaattttgaa cgtgcaaaaa aagctcccaa tcatccaaaa aattattatc   1980

atggattcta aaacggatta ccagggattt cagtcgatgt acacgttcgt cacatctcat   2040

ctacctcccg gttttaatga atacgatttt gtgccagagt ccttcgatag ggacaagaca   2100

attgcactga tcatgaactc ctctggatct actggtctgc ctaaaggtgt cgctctgcct   2160

catagaactg cctgcgtgag attctcgcat gccagagatc ctatttttgg caatcaaatc   2220

attccggata ctgcgatttt aagtgttgtt ccattccatc acggttttgg aatgtttact   2280

acactcggat atttgatatg tggatttcga gtcgtcttaa tgtatagatt tgaagaagag   2340

ctgtttctga ggagccttca ggattacaag attcaaagtg cgctgctggt gccaacccta   2400

ttctccttct tcgccaaaag cactctgatt gacaaatacg atttatctaa tttacacgaa   2460

attgcttctg gtggcgctcc cctctctaag gaagtcgggg aagcggttgc caagaggttc   2520

catctgccag gtatcaggca aggatatggg ctcactgaga ctacatcagc tattctgatt   2580

acacccgagg gggatgataa accgggcgcg gtcggtaaag ttgttccatt ttttgaagcg   2640

aaggttgtgg atctggatac cgggaaaacg ctgggcgtta atcaaagagg cgaactgtgt   2700

gtgagaggtc ctatgattat gtccggttat gtaaacaatc cggaagcgac caacgccttg   2760

attgacaagg atggataa                                                 2778
```

<210> SEQ ID NO 13
<211> LENGTH: 925
<212> TYPE: PRT
<213> ORGANISM: Artificial
<220> FEATURE:
<223> OTHER INFORMATION: GID1C sensor peptide

<400> SEQUENCE: 13

```
Met Ser Gly Tyr Val Asn Asn Pro Glu Ala Thr Asn Ala Leu Ile Asp
1               5                   10                  15

Lys Asp Gly Trp Leu His Ser Gly Asp Ile Ala Tyr Trp Asp Glu Asp
            20                  25                  30

Glu His Phe Phe Ile Val Asp Arg Leu Lys Ser Leu Ile Lys Tyr Lys
        35                  40                  45

Gly Tyr Gln Val Ala Pro Ala Glu Leu Glu Ser Ile Leu Leu Gln His
    50                  55                  60

Pro Asn Ile Phe Asp Ala Gly Val Ala Gly Leu Pro Asp Asp Asp Ala
65                  70                  75                  80
```

-continued

```
Gly Glu Leu Pro Ala Ala Val Val Val Leu Glu His Gly Lys Thr Met
                85                  90                  95

Thr Glu Lys Glu Ile Val Asp Tyr Val Ala Ser Gln Val Thr Thr Ala
            100                 105                 110

Lys Lys Leu Arg Gly Gly Val Val Phe Val Asp Glu Val Pro Lys Gly
        115                 120                 125

Leu Thr Gly Lys Leu Asp Ala Arg Lys Ile Arg Glu Ile Leu Ile Lys
    130                 135                 140

Ala Lys Lys Gly Gly Lys Ile Ala Val Gly Gly Gly Gly Gly Gly Gly
145                 150                 155                 160

Ala Gly Ser Glu Glu Val Asn Leu Ile Glu Ser Lys Thr Val Val Pro
                165                 170                 175

Leu Asn Thr Trp Val Leu Ile Ser Asn Phe Lys Leu Ala Tyr Asn Leu
            180                 185                 190

Leu Arg Arg Pro Asp Gly Thr Phe Asn Arg His Leu Ala Glu Phe Leu
        195                 200                 205

Asp Arg Lys Val Pro Ala Asn Ala Asn Pro Val Asn Gly Val Phe Ser
    210                 215                 220

Phe Asp Val Ile Ile Asp Arg Gln Thr Asn Leu Leu Ser Arg Val Tyr
225                 230                 235                 240

Arg Pro Ala Asp Ala Gly Thr Ser Pro Ser Ile Thr Asp Leu Gln Asn
                245                 250                 255

Pro Val Asp Gly Glu Ile Val Pro Val Ile Val Phe Phe His Gly Gly
            260                 265                 270

Ser Phe Ala His Ser Ser Ala Asn Ser Ala Ile Tyr Asp Thr Leu Cys
        275                 280                 285

Arg Arg Leu Val Gly Leu Cys Gly Ala Val Val Val Ser Val Asn Tyr
    290                 295                 300

Arg Arg Ala Pro Glu Asn Arg Tyr Pro Cys Ala Tyr Asp Asp Gly Trp
305                 310                 315                 320

Ala Val Leu Lys Trp Val Asn Ser Ser Ser Trp Leu Arg Ser Lys Lys
                325                 330                 335

Asp Ser Lys Val Arg Ile Phe Leu Ala Gly Asp Ser Ser Gly Gly Asn
            340                 345                 350

Ile Val His Asn Val Ala Val Arg Ala Val Glu Ser Arg Ile Asp Val
        355                 360                 365

Leu Gly Asn Ile Leu Leu Asn Pro Met Phe Gly Gly Thr Glu Arg Thr
    370                 375                 380

Glu Ser Glu Lys Arg Leu Asp Gly Lys Tyr Phe Val Thr Val Arg Asp
385                 390                 395                 400

Arg Asp Trp Tyr Trp Arg Ala Phe Leu Pro Glu Gly Glu Asp Arg Glu
                405                 410                 415

His Pro Ala Cys Ser Pro Phe Gly Pro Arg Ser Lys Ser Leu Glu Gly
            420                 425                 430

Leu Ser Phe Pro Lys Ser Leu Val Val Val Ala Gly Leu Asp Leu Ile
        435                 440                 445

Gln Asp Trp Gln Leu Lys Tyr Ala Glu Gly Leu Lys Lys Ala Gly Gln
    450                 455                 460

Glu Val Lys Leu Leu Tyr Leu Glu Gln Ala Thr Ile Gly Phe Tyr Leu
465                 470                 475                 480

Leu Pro Asn Asn Asn His Phe His Thr Val Met Asp Glu Ile Ala Ala
                485                 490                 495

Phe Val Asn Ala Glu Cys Gln Gly Gly Gly Gly Gly Gly Gly Glu Asp
```

-continued

```
            500                 505                 510

Ala Lys Asn Ile Lys Lys Gly Pro Ala Pro Phe Tyr Pro Leu Glu Asp
        515                 520                 525

Gly Thr Ala Gly Glu Gln Leu His Lys Ala Met Lys Arg Tyr Ala Leu
    530                 535                 540

Val Pro Gly Thr Ile Ala Phe Thr Asp Ala His Ile Glu Val Asp Ile
545                 550                 555                 560

Thr Tyr Ala Glu Tyr Phe Glu Met Ser Val Arg Leu Ala Glu Ala Met
                565                 570                 575

Lys Arg Tyr Gly Leu Asn Thr Asn His Arg Ile Val Val Cys Ser Glu
            580                 585                 590

Asn Ser Leu Gln Phe Phe Met Pro Val Leu Gly Ala Leu Phe Ile Gly
        595                 600                 605

Val Ala Val Ala Pro Ala Asn Asp Ile Tyr Asn Glu Arg Glu Leu Leu
    610                 615                 620

Asn Ser Met Gly Ile Ser Gln Pro Thr Val Val Phe Val Ser Lys Lys
625                 630                 635                 640

Gly Leu Gln Lys Ile Leu Asn Val Gln Lys Lys Leu Pro Ile Ile Gln
                645                 650                 655

Lys Ile Ile Ile Met Asp Ser Lys Thr Asp Tyr Gln Gly Phe Gln Ser
            660                 665                 670

Met Tyr Thr Phe Val Thr Ser His Leu Pro Pro Gly Phe Asn Glu Tyr
        675                 680                 685

Asp Phe Val Pro Glu Ser Phe Asp Arg Asp Lys Thr Ile Ala Leu Ile
    690                 695                 700

Met Asn Ser Ser Gly Ser Thr Gly Leu Pro Lys Gly Val Ala Leu Pro
705                 710                 715                 720

His Arg Thr Ala Cys Val Arg Phe Ser His Ala Arg Asp Pro Ile Phe
                725                 730                 735

Gly Asn Gln Ile Ile Pro Asp Thr Ala Ile Leu Ser Val Val Pro Phe
            740                 745                 750

His His Gly Phe Gly Met Phe Thr Thr Leu Gly Tyr Leu Ile Cys Gly
        755                 760                 765

Phe Arg Val Val Leu Met Tyr Arg Phe Glu Glu Glu Leu Phe Leu Arg
    770                 775                 780

Ser Leu Gln Asp Tyr Lys Ile Gln Ser Ala Leu Leu Val Pro Thr Leu
785                 790                 795                 800

Phe Ser Phe Phe Ala Lys Ser Thr Leu Ile Asp Lys Tyr Asp Leu Ser
                805                 810                 815

Asn Leu His Glu Ile Ala Ser Gly Gly Ala Pro Leu Ser Lys Glu Val
            820                 825                 830

Gly Glu Ala Val Ala Lys Arg Phe His Leu Pro Gly Ile Arg Gln Gly
        835                 840                 845

Tyr Gly Leu Thr Glu Thr Thr Ser Ala Ile Leu Ile Thr Pro Glu Gly
    850                 855                 860

Asp Asp Lys Pro Gly Ala Val Gly Lys Val Val Pro Phe Phe Glu Ala
865                 870                 875                 880

Lys Val Val Asp Leu Asp Thr Gly Lys Thr Leu Gly Val Asn Gln Arg
                885                 890                 895

Gly Glu Leu Cys Val Arg Gly Pro Met Ile Met Ser Gly Tyr Val Asn
            900                 905                 910

Asn Pro Glu Ala Thr Asn Ala Leu Ile Asp Lys Asp Gly
        915                 920                 925
```

<210> SEQ ID NO 14
<211> LENGTH: 26
<212> TYPE: DNA
<213> ORGANISM: Artificial Sequence
<220> FEATURE:
<223> OTHER INFORMATION: Primer for amplification of GID1c cDNA

<400> SEQUENCE: 14
atggctggaa gtgaagaagt taatct 26

<210> SEQ ID NO 15
<211> LENGTH: 21
<212> TYPE: DNA
<213> ORGANISM: Artificial Sequence
<220> FEATURE:
<223> OTHER INFORMATION: Primer for amplification of GID1c cDNA

<400> SEQUENCE: 15
tcattggcat tctgcgttta c 21

<210> SEQ ID NO 16
<211> LENGTH: 57
<212> TYPE: DNA
<213> ORGANISM: Artificial Sequence
<220> FEATURE:
<223> OTHER INFORMATION: Primer for Addition of linker to C-terminal domain of firefly luciferase

<400> SEQUENCE: 16
gattaacttc ttcacttcca gctcctccgc cacccccgcc acccacggcg atctttc 57

<210> SEQ ID NO 17
<211> LENGTH: 31
<212> TYPE: DNA
<213> ORGANISM: Artificial Sequence
<220> FEATURE:
<223> OTHER INFORMATION: Primer for Addition of linker to GID1c cDNA

<400> SEQUENCE: 17
ggcggaggag ctggaagtga agaagttaat c 31

<210> SEQ ID NO 18
<211> LENGTH: 27
<212> TYPE: DNA
<213> ORGANISM: Artificial Sequence
<220> FEATURE:
<223> OTHER INFORMATION: Primer for Addition of linker to GID1c cDNA

<400> SEQUENCE: 18
gcctccacct tggcattctg cgtttac 27

<210> SEQ ID NO 19
<211> LENGTH: 54
<212> TYPE: DNA
<213> ORGANISM: Artificial Sequence
<220> FEATURE:
<223> OTHER INFORMATION: Primer for Addition of linker to N-terminal domain firefly luciferase

<400> SEQUENCE: 19
gtaaacgcag aatgccaagg tggaggcgga ggcggaggcg aagacgccaa aaac 54

<210> SEQ ID NO 20
<211> LENGTH: 21
<212> TYPE: DNA

<213> ORGANISM: Artificial Sequence
<220> FEATURE:
<223> OTHER INFORMATION: Primer for amplification of N-terminal domain of firefly luciferase being non-overlapping

<400> SEQUENCE: 20
ttaaatcata ggacctctca c 21

<210> SEQ ID NO 21
<211> LENGTH: 21
<212> TYPE: DNA
<213> ORGANISM: Artificial Sequence
<220> FEATURE:
<223> OTHER INFORMATION: Primer for introduction of V53A mutation into GID1b by PCR amplification

<400> SEQUENCE: 21
ccgtaaagcc cccgccaact c 21

<210> SEQ ID NO 22
<211> LENGTH: 25
<212> TYPE: DNA
<213> ORGANISM: Artificial Sequence
<220> FEATURE:
<223> OTHER INFORMATION: Primer for Introduction of V53A mutation into GID1b by PCR amplification

<400> SEQUENCE: 22
ggcgggggct ttacggtcaa ggaac 25

<210> SEQ ID NO 23
<211> LENGTH: 19
<212> TYPE: DNA
<213> ORGANISM: Artificial Sequence
<220> FEATURE:
<223> OTHER INFORMATION: Primer for DELLA protein GAI gene PCR amplification, without ATG

<400> SEQUENCE: 23
aagagagatc atcatcatc 19

<210> SEQ ID NO 24
<211> LENGTH: 23
<212> TYPE: DNA
<213> ORGANISM: Artificial Sequence
<220> FEATURE:
<223> OTHER INFORMATION: Primer for DELLA protein GAI gene PCR amplification

<400> SEQUENCE: 24
ctaattggtg gagagtttcc aag 23

<210> SEQ ID NO 25
<211> LENGTH: 2820
<212> TYPE: DNA
<213> ORGANISM: Artificial Sequence
<220> FEATURE:
<223> OTHER INFORMATION: GID1B.5 sensor nucleotide sequence

<400> SEQUENCE: 25
atgtccggtt atgtaaacaa tccggaagcg accaacgcct tgattgacaa ggatggatgg 60
ctacattctg gagacatagc ttactgggac gaagacgaac acttcttcat cgttgaccgc 120
ctgaagtctc tgattaagta caaaggctat caggtggctc ccgctgaatt ggaatccatc 180
ttgctccaac accccaacat cttcgacgca ggtgtcgcag gtcttcccga cgatgacgcc 240

-continued

```
ggtgaacttc ccgccgccgt tgttgttttg gagcacggaa agacgatgac ggaaaaagag    300
atcgtggatt acgtcgccag tcaagtaaca accgcgaaaa agttgcgcgg aggagttgtg    360
tttgtggacg aagtaccgaa aggtcttacc ggaaaactcg acgcaagaaa aatcagagag    420
atcctcataa aggccaagaa gggcggaaag atcgccgtgg gtggcggggg tggcggagga    480
gctggtggta acgaagtcaa ccttaacgaa tgcaagagaa ttgtcccact caacacatgg    540
gtcctcattt ccaatttcaa gcttgcttac aaagtcctcc gtcgccctga cggttctttc    600
aaccgcgacc tcgccgagtt ccttgaccgt aaagcccccg ccaactcttt ccccctcgac    660
ggcgttttct ccttcgacca cgtcgactca acaactaacc ttctcaccag aatctaccaa    720
cctgcgtctc tccttcatca gacccgtcac ggaaccctcg agctaaccaa acctctcagt    780
actacagaga tcgtccctgt tctcattttc ttccatggag gcagcttcac tcattcctcc    840
gccaatagtg ctatctacga cactttctgc cgacgccttg tcaccatttg cggtgttgtt    900
gttgtctctg ttgattaccg gagatcccct gagcatcgct acccttgtgc ttacgacgat    960
ggatggaacg ctctcaactg ggtcaagtcc agagtctggc ttcagagtgg taaagactcc   1020
aatgtttatg tttatttggc tggagatagc tctggaggca acattgctca caatgtcgct   1080
gtcagagcta ccaatgaagg agtcaaagtg ttggggaaca ttcttcttca tccaatgttt   1140
ggtggacagg agaggactca gtctgagaag acccttgatg gcaaatactt tgtgactata   1200
caagatcgag attggtattg gagggcttat ctaccggaag gtgaagatag agatcatcca   1260
gcatgtaatc cctttggccc gagaggtcaa agccttaaag gagtcaactt tccaaagagt   1320
cttgttgttg tcgctggttt agatcttgtt caagattggc aattagccta tgtggatggg   1380
cttaagaaga ctggtcttga agtcaatctt ttgtatttga aacaagctac cattggcttt   1440
tacttcttgc ctaacaatga tcactttcat tgtcttatgg aagagttgaa taagtttgtg   1500
cactccatag aggattctca aagcaagtca agtcctgtgc ttcttactcc tggtggaggc   1560
ggaggcggag gcgaagacgc caaaaacata aagaaaggcc cggcgccatt ctatccgctg   1620
gaagatggaa ccgctggaga gcaactgcat aaggctatga agagatacgc cctggttcct   1680
ggaacaattg cttttacaga tgcacatatc gaggtggaca tcacttacgc tgagtacttc   1740
gaaatgtccg ttcggttggc agaagctatg aaacgatatg ggctgaatac aaatcacaga   1800
atcgtcgtat gcagtgaaaa ctctcttcaa ttctttatgc cggtgttggg cgcgttattt   1860
atcggagttg cagttgcgcc cgcgaacgac atttataatg aacgtgaatt gctcaacagt   1920
atgggcattt cgcagcctac cgtggtgttc gtttccaaaa aggggttgca aaaaattttg   1980
aacgtgcaaa aaaagctccc aatcatccaa aaaattatta tcatggattc taaaacggat   2040
taccagggat ttcagtcgat gtacacgttc gtcacatctc atctacctcc cggttttaat   2100
gaatacgatt ttgtgccaga gtccttcgat agggacaaga caattgcact gatcatgaac   2160
tcctctggat ctactggtct gcctaaaggt gtcgctctgc ctcatagaac tgcctgcgtg   2220
agattctcgc atgccagaga tcctattttt ggcaatcaaa tcattccgga tactgcgatt   2280
ttaagtgttg ttccattcca tcacggtttt ggaatgttta ctacactcgg atatttgata   2340
tgtggatttc gagtcgtctt aatgtataga tttgaagaag agctgtttct gaggagcctt   2400
caggattaca agattcaaag tgcgctgctg gtgccaaccc tattctcctt cttcgccaaa   2460
agcactctga ttgacaaata cgatttatct aatttacacg aaattgcttc tggtggcgct   2520
cccctctcta aggaagtcgg ggaagcggtt gccaagaggt tccatctgcc aggtatcagg   2580
caaggatatg ggctcactga gactacatca gctattctga ttacacccga gggggatgat   2640
```

```
aaaccgggcg cggtcggtaa agttgttcca ttttttgaag cgaaggttgt ggatctggat   2700

accgggaaaa cgctgggcgt taatcaaaga ggcgaactgt gtgtgagagg tcctatgatt   2760

atgtccggtt atgtaaacaa tccggaagcg accaacgcct tgattgacaa ggatggataa   2820


<210> SEQ ID NO 26
<211> LENGTH: 939
<212> TYPE: PRT
<213> ORGANISM: Artificial Sequence
<220> FEATURE:
<223> OTHER INFORMATION: GID1B.5 sensor protein sequence

<400> SEQUENCE: 26

Met Ser Gly Tyr Val Asn Asn Pro Glu Ala Thr Asn Ala Leu Ile Asp
1               5                   10                  15

Lys Asp Gly Trp Leu His Ser Gly Asp Ile Ala Tyr Trp Asp Glu Asp
            20                  25                  30

Glu His Phe Phe Ile Val Asp Arg Leu Lys Ser Leu Ile Lys Tyr Lys
        35                  40                  45

Gly Tyr Gln Val Ala Pro Ala Glu Leu Glu Ser Ile Leu Leu Gln His
    50                  55                  60

Pro Asn Ile Phe Asp Ala Gly Val Ala Gly Leu Pro Asp Asp Asp Ala
65                  70                  75                  80

Gly Glu Leu Pro Ala Ala Val Val Val Leu Glu His Gly Lys Thr Met
                85                  90                  95

Thr Glu Lys Glu Ile Val Asp Tyr Val Ala Ser Gln Val Thr Thr Ala
            100                 105                 110

Lys Lys Leu Arg Gly Gly Val Val Phe Val Asp Glu Val Pro Lys Gly
        115                 120                 125

Leu Thr Gly Lys Leu Asp Ala Arg Lys Ile Arg Glu Ile Leu Ile Lys
    130                 135                 140

Ala Lys Lys Gly Gly Lys Ile Ala Val Gly Gly Gly Gly Gly Gly Gly
145                 150                 155                 160

Ala Gly Gly Asn Glu Val Asn Leu Asn Glu Cys Lys Arg Ile Val Pro
                165                 170                 175

Leu Asn Thr Trp Val Leu Ile Ser Asn Phe Lys Leu Ala Tyr Lys Val
            180                 185                 190

Leu Arg Arg Pro Asp Gly Ser Phe Asn Arg Asp Leu Ala Glu Phe Leu
        195                 200                 205

Asp Arg Lys Ala Pro Ala Asn Ser Phe Pro Leu Asp Gly Val Phe Ser
    210                 215                 220

Phe Asp His Val Asp Ser Thr Thr Asn Leu Leu Thr Arg Ile Tyr Gln
225                 230                 235                 240

Pro Ala Ser Leu Leu His Gln Thr Arg His Gly Thr Leu Glu Leu Thr
                245                 250                 255

Lys Pro Leu Ser Thr Thr Glu Ile Val Pro Val Leu Ile Phe Phe His
            260                 265                 270

Gly Gly Ser Phe Thr His Ser Ser Ala Asn Ser Ala Ile Tyr Asp Thr
        275                 280                 285

Phe Cys Arg Arg Leu Val Thr Ile Cys Gly Val Val Val Val Ser Val
    290                 295                 300

Asp Tyr Arg Arg Ser Pro Glu His Arg Tyr Pro Cys Ala Tyr Asp Asp
305                 310                 315                 320

Gly Trp Asn Ala Leu Asn Trp Val Lys Ser Arg Val Trp Leu Gln Ser
                325                 330                 335
```

-continued

```
Gly Lys Asp Ser Asn Val Tyr Val Tyr Leu Ala Gly Asp Ser Ser Gly
            340                 345                 350

Gly Asn Ile Ala His Asn Val Ala Val Arg Ala Thr Asn Glu Gly Val
        355                 360                 365

Lys Val Leu Gly Asn Ile Leu Leu His Pro Met Phe Gly Gly Gln Glu
    370                 375                 380

Arg Thr Gln Ser Glu Lys Thr Leu Asp Gly Lys Tyr Phe Val Thr Ile
385                 390                 395                 400

Gln Asp Arg Asp Trp Tyr Trp Arg Ala Tyr Leu Pro Glu Gly Glu Asp
                405                 410                 415

Arg Asp His Pro Ala Cys Asn Pro Phe Gly Pro Arg Gly Gln Ser Leu
            420                 425                 430

Lys Gly Val Asn Phe Pro Lys Ser Leu Val Val Val Ala Gly Leu Asp
        435                 440                 445

Leu Val Gln Asp Trp Gln Leu Ala Tyr Val Asp Gly Leu Lys Lys Thr
    450                 455                 460

Gly Leu Glu Val Asn Leu Leu Tyr Leu Lys Gln Ala Thr Ile Gly Phe
465                 470                 475                 480

Tyr Phe Leu Pro Asn Asn Asp His Phe His Cys Leu Met Glu Glu Leu
                485                 490                 495

Asn Lys Phe Val His Ser Ile Glu Asp Ser Gln Ser Lys Ser Ser Pro
            500                 505                 510

Val Leu Leu Thr Pro Gly Gly Gly Gly Gly Gly Gly Glu Asp Ala Lys
        515                 520                 525

Asn Ile Lys Lys Gly Pro Ala Pro Phe Tyr Pro Leu Glu Asp Gly Thr
    530                 535                 540

Ala Gly Glu Gln Leu His Lys Ala Met Lys Arg Tyr Ala Leu Val Pro
545                 550                 555                 560

Gly Thr Ile Ala Phe Thr Asp Ala His Ile Glu Val Asp Ile Thr Tyr
                565                 570                 575

Ala Glu Tyr Phe Glu Met Ser Val Arg Leu Ala Glu Ala Met Lys Arg
            580                 585                 590

Tyr Gly Leu Asn Thr Asn His Arg Ile Val Val Cys Ser Glu Asn Ser
        595                 600                 605

Leu Gln Phe Phe Met Pro Val Leu Gly Ala Leu Phe Ile Gly Val Ala
    610                 615                 620

Val Ala Pro Ala Asn Asp Ile Tyr Asn Glu Arg Glu Leu Leu Asn Ser
625                 630                 635                 640

Met Gly Ile Ser Gln Pro Thr Val Val Phe Val Ser Lys Lys Gly Leu
                645                 650                 655

Gln Lys Ile Leu Asn Val Gln Lys Lys Leu Pro Ile Ile Gln Lys Ile
            660                 665                 670

Ile Ile Met Asp Ser Lys Thr Asp Tyr Gln Gly Phe Gln Ser Met Tyr
        675                 680                 685

Thr Phe Val Thr Ser His Leu Pro Pro Gly Phe Asn Glu Tyr Asp Phe
    690                 695                 700

Val Pro Glu Ser Phe Asp Arg Asp Lys Thr Ile Ala Leu Ile Met Asn
705                 710                 715                 720

Ser Ser Gly Ser Thr Gly Leu Pro Lys Gly Val Ala Leu Pro His Arg
                725                 730                 735

Thr Ala Cys Val Arg Phe Ser His Ala Arg Asp Pro Ile Phe Gly Asn
            740                 745                 750
```

-continued

```
Gln Ile Ile Pro Asp Thr Ala Ile Leu Ser Val Val Pro Phe His His
        755                 760                 765

Gly Phe Gly Met Phe Thr Thr Leu Gly Tyr Leu Ile Cys Gly Phe Arg
    770                 775                 780

Val Val Leu Met Tyr Arg Phe Glu Glu Glu Leu Phe Leu Arg Ser Leu
785                 790                 795                 800

Gln Asp Tyr Lys Ile Gln Ser Ala Leu Leu Val Pro Thr Leu Phe Ser
                805                 810                 815

Phe Phe Ala Lys Ser Thr Leu Ile Asp Lys Tyr Asp Leu Ser Asn Leu
            820                 825                 830

His Glu Ile Ala Ser Gly Gly Ala Pro Leu Ser Lys Glu Val Gly Glu
        835                 840                 845

Ala Val Ala Lys Arg Phe His Leu Pro Gly Ile Arg Gln Gly Tyr Gly
    850                 855                 860

Leu Thr Glu Thr Thr Ser Ala Ile Leu Ile Thr Pro Glu Gly Asp Asp
865                 870                 875                 880

Lys Pro Gly Ala Val Gly Lys Val Val Pro Phe Phe Glu Ala Lys Val
                885                 890                 895

Val Asp Leu Asp Thr Gly Lys Thr Leu Gly Val Asn Gln Arg Gly Glu
            900                 905                 910

Leu Cys Val Arg Gly Pro Met Ile Met Ser Gly Tyr Val Asn Asn Pro
        915                 920                 925

Glu Ala Thr Asn Ala Leu Ile Asp Lys Asp Gly
    930                 935
```

SENSOR PEPTIDE AND METHODS OF USE THEREOF TO IDENTIFY SUBSTANCES THAT MODULATE GIBBERELLIC ACID ACTION

The present invention relates to methods of identifying substances that modulate the action of plant hormones of the gibberellin class by targeting receptors of the GID1 class using GID1 based sensor peptides. The present invention furthermore relates to substances acting as gibberellin analogs or antagonists that target GID1 receptors. The present invention furthermore relates to sensor peptides especially designed for such methods as well as a strain of the species *Saccharomyces cerevisiae* expressing such a GID1 based sensor peptide.

Gibberellins constitute one of the major classes of plant hormones. The first gibberellin to be structurally characterized was gibberellic acid, $GA_3$, from the fungal pathogen *Gibberella fujikuroi*. After gibberellic acid, gibberellins are often referred to as GAs, and different GA isoforms are known as $GA_1$, $GA_2$, $GA_3$ and so on. Henceforth, gibberellins in this text are referred to collectively as GA.

As with other hormones, GA action relies on its perception by its receptor(s). While in rice there is only one GA receptor encoded by the gene GIBBERELLIN-INSENSITIVE DWARF1 (GID1), the model plant *Arabidopsis thaliana* has three genes encoding GID1 homologous proteins, GID1A-C; collectively, these are henceforth referred to as GID1. It has been suggested that upon GA binding the GID1 receptor changes its conformation. Such a conformational change has been proposed to lead to the interaction and targeted degradation of a set of negative regulators of GA action, the DELLA family of proteins. GID1-mediated degradation of DELLA proteins triggers the GA transduction pathway. As with most plant hormones, GA homeostasis is tightly regulated by the role of enzymes that convert the pool of biologically inactive GA isoforms to the active isoforms that can induce GA responses. Another group of enzymes is responsible for inactivating active isoforms, to limit the duration of the GA response.

So far, attempts to localize active forms of GA in cells and developing plants have relied on the indirect assessment of the expression of GA metabolic and catabolic enzymes, or the laborious and challenging measurement of GA levels by biochemical methods. Such methods not only lack dynamic spatial-temporal resolution, but are also limited by the amount of plant material required.

Ueguchi-Tanaka et al. (Plant Cell, 2007; 19; pages 2140-55) describe studies of molecular mechanism for GA binding to the GID1 receptor and GA-dependent interaction between GID1 and the DELLA protein SLR1. For studying the GA-dependent interaction between GID1 and SLR1 the authors used a biomolecular fluorescence complementation assay. Here two different fusion proteins were used as sensors, wherein each comprises an inactive fragment of a fluorescence protein that its own is non-fluorescent and a full-length plant protein to be tested for interaction with another, different full-length plant protein. Interaction between the two fusion proteins and therefore of the fragments restores the function of the inactive fluorescence protein fragments because of physical proximity. In this assay, molecular proximity of GID1 and SLR1 in plants was dependent on $GA_4$. As can be seen from FIG. 10 of Ueguchi-Tanaka et al. (Plant Cell, 2007), the authors suggest an interaction model based on a receptor conformational change upon substrate binding based on the similarity of GID1 to hormone-sensitive lipases. In this suggested model, binding of GA to GID1 causes conformational changes of GID1 that are stabilized by additional binding of SLR1. Importantly, no conformational change is demonstrated, but only proposed. This is but one of many possible models to explain the reported data, and a conformational change of GID1 is not necessary to explain the reported data. It is only shown that the strength of interaction between GID1 and SLR1 is dependent of the presence of GA. Furthermore, this is in direct contradiction to the model of Hao et al. (Journal of Computational Chemistry 2013, 34, 2055-2064), in which arguments against a conformational change of GID1 upon binding to GA are presented.

Furthermore, Ueguchi-Tanaka et al. (Plant Cell, 2007) does not describe an assay operating with only one sensor peptide comprising the C-terminal domain of a bioluminescent reporter followed by a first linker, a GA receptor, a second linker and a N-terminal domain of the bioluminescent reporter. Thus, the present invention differs from their assay and is novel. The assay of the present invention is focused on binding of GA or GA functional analogs to a receptor of the GID1 class. Therefore, the inventive assay refers not only to identification of interactions between different proteins, but also to interaction between different parts of the same protein and identification of protein-small molecule interactions that modulate the intraprotein interactions. In the assay of Ueguchi-Tanaka et al. (Plant Cell, 2007) two different constructs were used, each construct comprising a different protein of interest and an inactive fragment of a reporter. To use only one sensor peptide instead of two constructs comprising two different proteins as used in a conventional fluorescence protein complementation assay is only possible because the inventors found that the conformational change of GA receptors have special characteristics. Furthermore, usage of the inventive sensors is clearly advantageous compared to the sensor pair of Ueguchi-Tanaka et al. After successful construction of one specific sensor peptide a library of possible binding partners (such as small molecules) may be screened for binding to GID1 receptors, without preparation of a fusion protein for each candidate substance. Furthermore, the assay of the present invention enables not only the detection of binding but also the validation that the binding causes a conformational change of the receptor, which is a strong indication of functionally adequate interaction between GA and its receptor. The assay is further independent of GID1 interaction with members of the DELLA family such as SLR1. Furthermore, the present invention is not obvious, also not with the presumption that GID1 receptor shows a conformational change. Ueguchi-Tanaka et al. (Plant Cell, 2007) does not teach which portions of the GA receptor may interact with each other. Ueguchi-Tanaka et al. (Plant Cell, 2007) therefore does not teach how inactive fragments of a fluorescent or luminescent reporter need to be attached to a GA receptor in order to elicit fluorescence or luminescence after binding of the GA receptor to GA. That the conformational change of GID1 is suitable to restore functionality of two inactive fragments of a reporter such as luciferase or a fluorescent protein attached to the ends of the receptor thus is not apparent from the state of the art.

It is the objective of the present invention to provide a molecular sensor able to quantitatively report in vivo the spatial-temporal localization of active GA isoforms. It is another objective of the present invention to provide an assay to identify substances that modulate GA action, including inhibition or activation of GA signaling.

The objective of the present invention is solved by the teaching of the independent claims. Further advantageous features, aspects and details of the invention are evident from the dependent claims, the description, the figures, and the examples of the present application.

The present invention provides methods of identifying substances that modulate GA action through targeting its receptor or acting as a GA functional analog comprising the following steps:

a) providing a candidate substance to be tested,
b) providing a sensor peptide,
c) bringing the candidate substance into contact with the sensor peptide,
d) providing conditions sufficient to allow the candidate substance to bind to the sensor peptide,
e) determining whether the candidate substance binds to the sensor peptide, wherein the sensor peptide encompasses at its N-terminus domain a first inactive fragment of a bioluminescent reporter or of a fluorescent reporter followed by a first linker, a GA receptor of the GID1 family, a second linker and at its C-terminus domain a second inactive fragment of the bioluminescent reporter or of the fluorescent reporter and wherein the first and the second inactive fragment of the bioluminescent reporter or of the fluorescent reporter are suitable to restore functionality of the bioluminescent reporter or of the fluorescent reporter. Thereby, functionality of the bioluminescent reporter or of the fluorescent reporter means bioluminescence or respectively fluorescence.

It is preferred that the bioluminescent reporter or the fluorescent reporter are a peptide or a protein, hence, that the sensor peptide comprises only amino acids and is a fusion protein encompassing the inactive bioluminescent or fluorescent reporter fragments, two linkers and the receptor, Therefore, one preferred embodiment of the present invention are methods of identifying substances that modulate GA action through targeting its receptor or acting as a GA functional analog comprising the following steps:

a) providing a candidate substance to be tested,
b) providing a sensor peptide,
c) bringing the candidate substance into contact with the sensor peptide,
d) providing conditions sufficient to allow the candidate substance to bind to the sensor peptide,
e) determining whether the candidate substance binds to the sensor peptide, wherein the sensor peptide encompasses at its N-terminus a C-terminal domain of a bioluminescent reporter or of a fluorescent reporter followed by a first linker, a GA receptor of the GID1 family, a second linker and at its C-terminus a N-terminal domain of the bioluminescent reporter or of the fluorescent reporter wherein the N- and C-terminal domain of the fluorescent reporter are suitable to restore bioluminescence or fluorescence respectively. Thereby it is further preferred that the N- and C-terminal domains of the bioluminescent reporter or of the fluorescent reporter protein in the peptide have an overlap of 10-30 amino acids.

Another aspect of the present invention refers to methods of identifying substances that modulate GA action through targeting its receptor or acting as a GA functional analog comprising the following steps:

a) providing a candidate substance to be tested,
b) providing a sensor peptide,
c) bringing the candidate substance into contact with the sensor peptide,
d) providing conditions sufficient to allow the candidate substance to bind to the sensor peptide,
e) determining whether the candidate substance binds to the sensor peptide, wherein the sensor peptide encompasses at its N-terminus a C-terminal domain of a bioluminescent reporter followed by a first linker, a GA receptor, a second linker and at its C-terminus a N-terminal domain of the bioluminescent reporter and wherein the N- and C-terminal domains of the bioluminescent reporter in the peptide have an overlap of 10-30 amino acids.

One preferred embodiment of the present invention refers to methods of identifying substances that modulate GA action through targeting a GID1 receptor or acting as a GA functional analog comprising the following steps:

a) providing a candidate substance to be tested,
b) providing a sensor peptide,
c) bringing the candidate substance into contact with the sensor peptide,
d) providing conditions sufficient to allow the candidate substance to bind to the sensor peptide,
e) determining whether the candidate substance binds to the sensor peptide, wherein the sensor peptide encompasses at its N-terminus a C-terminal domain of a bioluminescent reporter followed by a first linker, a GA receptor of the GID1 family, a second linker and at its C-terminus a N-terminal domain of the bioluminescent reporter and wherein the N- and C-terminal domains of the bioluminescent reporter in the peptide have an overlap of 10-30 amino acids.

The term "bioluminescent reporter" as used herein refers to any kind of oxidative enzyme creating chemiluminescence or bioluminescence when interacting with a luminogenic substrate. The overlap of the bioluminescent reporter allows a strategy of intramolecular complementation. The inventors could show that sensors without overlap show no bioluminescence (see FIG. 7). Preferably, the bioluminescent reporter is selected from the group comprising or consisting of: beetle luciferases (including firefly luciferase), Renilla-luciferin 2-monooxygenase (also called Renilla-type luciferase), color variants of firefly luciferase and aequorin. In particularly preferred embodiments the bioluminescent reporter is firefly luciferase from the firefly *Photinus pyralis.*

Thus, preferred embodiments of the present invention are methods for identifying substances that modulate GA action through targeting a GID1 receptor or acting as a GA functional analog comprising the following steps:

a) providing a candidate substance to be tested,
b) providing a sensor peptide,
c) bringing the candidate substance into contact with the sensor peptide,
d) providing conditions sufficient to allow the candidate substance to bind to the sensor peptide,
e) determining whether the candidate substance binds to the sensor peptide, wherein the sensor is a peptide encompassing at its N-terminus a sequence that is at least 90% identical with amino acids 397-550 of the firefly luciferase according to SEQ ID No. 1 followed by a first linker, a GA receptor of the GID1 family, a second linker and at its C-terminus a sequence that is at least 90% identical with amino acids 1-416 of the firefly luciferase according to SEQ ID No. 1.

Another embodiment of the present invention refers to methods of identifying substances that modulate GA action through targeting its receptor or acting as a GA functional analog comprising the following steps:

a) providing a candidate substance to be tested,
b) providing a sensor peptide,
c) bringing the candidate substance into contact with the sensor peptide, d) providing conditions sufficient to allow the candidate substance to bind to the sensor peptide, e) determining whether the candidate substance binds to the sensor peptide, wherein the sensor peptide encompasses at its N-terminus a first inactive fragment of a fluorescent reporter followed by a first linker, a GA receptor of the GID1 family, a second linker and at its C-terminus a second inactive fragment of the fluorescent reporter wherein the first and the second inactive fragment of the fluorescent reporter are together suitable to restore fluorescence of the reporter (due to conformational change of the GA receptor upon binding of the candidate substance). Fluorescent proteins wherein the first inactive fragment is a N-terminal domain and the second inactive fragment is a C-terminal domain of the fluorescent protein are preferably used as the fluorescent reporter. It is further preferred that these N- and C-terminal domains of the fluorescence protein in the sensor peptide have an overlap of 10-30 amino acids.

Yet, another preferred embodiment of the present invention refers to methods of identifying substances that modulate GA action through targeting its receptor or acting as a GA functional analog comprising the following steps:

a) providing a candidate substance to be tested, b) providing a sensor peptide, c) bringing the candidate substance into contact with the sensor peptide, d) providing conditions sufficient to allow the candidate substance to bind to the sensor peptide, e) determining whether the candidate substance binds to the sensor peptide, wherein the sensor peptide encompasses at its N-terminus a C-terminal domain of a fluorescent reporter protein followed by a first linker, a GA receptor of the GID1 family, a second linker and at its C-terminus a N-terminal domain of the fluorescent reporter protein wherein the N- and C-terminal domain of the fluorescent reporter having an overlap of 10-30 amino acids are together suitable to restore fluorescence of the reporter (due to conformational change of the GA receptor upon binding of the candidate substance).

The term "fluorescent reporter" as used herein refers to a fluorescent chemical compound that absorbs light energy of a specific wavelength and re-emits light at a longer wavelength. Fluorophores typically contain several combined aromatic groups, or plane or cyclic molecules with several π bonds. The fluorophores are herein used as a dye for reporting conformational change of the receptor element of the sensor peptide. Preferred herein are fluorescent proteins such as GFP (green fluorescent protein), YFP (yellow fluorescent protein) and DsRed (red fluorescent protein) which can be attached to other proteins, here the receptor of GID1 class to form a fusion protein, synthesized in cells after tranfection or transformation of a suitable plasmid carrier.

One can, in addition, use the principle of competitive binding assays by using a specific binding agent, such as a natural ligand, which competes for the binding to the sensor peptide in order to determine whether the candidate substance acts as a competitive GA antagonist. Such an antagonist would bind to the receptor (and the sensor peptide) at the same site as the natural ligands but would not activate the receptor, because it would not cause a conformational change of the receptor. Hence, optionally, the method described above comprises further the following steps:

f) adding a substance known to bind the sensor peptide such as a natural activating ligand of the used GA receptor, for example, $GA_3$ or $GA_4$ for GID1, and providing conditions sufficient to allow binding of the substance known to bind the sensor peptide and, g) determining whether the candidate substance is able to compete with the substance of step f) for binding to the sensor peptide.

Thereby step g) may also be part of step e) of the inventive method, when the substance known to bind the sensor peptide and thereby activating the receptor (causing a conformational change) is allowed to bind to the sensor peptide before step e) and preferably before step c) takes place. In general, but especially for the embodiment comprising steps f) and g), it is preferred to use the candidate substance in excess compared to the sensor peptide. The level of specific binding of the test substance may be determined in the presence of a range of concentrations of the test substance with constant concentration of competing compound (natural ligand), in order to measure the kinetics with which they compete for the binding. For competition-binding assays, the incubation time should be sufficiently long to reach binding equilibrium.

The candidate substance to be tested within a method of the invention for identifying substances that modulate GA action through targeting its receptor or acting as a GA functional analog may be any type of chemical molecule. Isolation and characterization of substances with the potential to modulate GA action may be of interest for agriculture or in order to find new tools for research to obtain further biological insights into processes regulated by GAs. The method of the present invention is suitable for screening large compound libraries for substances modulating GA action. Such compounds can, for example, result in increased crop growth and increased crop yield, they can result in, improvement of malting processes, they can positively influence other desirable traits, or they can act as herbicides.

In a preferred embodiment of the methods according to the invention the candidate substance can be:

i) a small molecule, ii) an aptamer, iii) a peptide, a protein, or a protein complex, iv) or an antibody.

The term small molecule refers to a low molecular weight organic compound, which is by definition not a polymer. In the field of pharmacology, it is usually restricted to a molecule that also binds with high affinity to biopolymers such as proteins, nucleic acids or polysaccharides. Small molecules are broadly used as enzyme inhibitors or analogs for ligands such as GAs.

Aptamers are oligonucleic acid (DNA or RNA aptamers) or peptide molecules (peptide aptamers) that bind to a specific target molecule. Aptamers can be used for therapeutic purposes as macromolecular drugs. Aptamers can be created by selection from a large random sequence pool.

Antibodies are vertebrate proteins that bind very specifically to antigens. They can be formed for virtually any structure and are thus valuable tools for direct interaction with certain molecules. Recombinant techniques can be used to generate antibodies and antibody fragments that basically consist of the binding moieties of the antibodies.

There are currently over 100 gibberellins identified from plants, fungi and bacteria. GAs are diterpenes synthesized from acetyl CoA. They all have either 19 or 20 carbon units grouped into either four or five ring systems.

Active GAs show many physiological effects and regulate major aspects of seed development and germination, plant growth, flowering, fertilization and fruit set and overall development. Therefore modulation of GA activity may have a major impact on agriculture. For example, DELLA proteins, which are negative regulators of GA signaling, are encoded by the genes that enabled the Green Revolution in the 1960s. The substance to be tested within the methods of the present invention may be suitable for modulating GA action, which means they may stimulate or inhibit GA action; both can be favorable depending on the plant and the GA action to be influenced.

The term "GA action" as used herein refers to any physiological process modulated by GAs, such as:

stem elongation by stimulating cell division and elongation,
bolting/flowering in response to long and short days,
breaking of seed dormancy in plants that require stratification or light for germination,
enzyme production (α-amylase) in germinating cereal grains for mobilization of seed reserves,
stamen development in dioecious flowers (sex expression),
parthenocarpic (seedless) fruit development,
senescence in leaves and fruits,
defense against pathogens,
defense against abiotic stresses, especially drought.

Herein the term "GA functional analog" refers to any molecule (such as peptides, small molecules or aptamers) that binds to a GA receptor and/or triggers a conformational change of the GA receptor, preferably in absence of any other binding partner. Thus, a "GA functional analog" is mimicking binding of GA in nature The present invention further provides methods for identifying substances that positively or negatively modulate GA action through targeting its receptor (preferably of the GID1 family) or acting as a GA functional analog comprising following steps a) to e):

a) providing a candidate substance to be tested,
b) providing a sensor peptide,
c) bringing the candidate substance into contact with the sensor peptide,
d) providing conditions sufficient to allow the candidate substance to bind to the sensor peptide, and
e) determining whether the candidate substance binds to the sensor peptide wherein the sensor peptide encompasses at its N-terminus a C-terminal domain of a bioluminescent reporter followed by a first linker, a GA receptor of the GID1 family, a second linker and at its C-terminus a N-terminal domain of the bioluminescent reporter and wherein the N- and C-terminal domains of the bioluminescent reporter in the peptide have an overlap of 10-30 amino acids.

Thereby "positively modulating" means that the candidate substance to be tested increases GA action or that the candidate substance to be tested acts as an analog of GA having increased action. An increased GA action thereby includes a longer lasting or amplified activation of GA signaling pathways.

"Negatively modulating" means that the candidate substance to be tested decreases GA action or that the candidate substance to be tested acts as an analog of GA having decreased action. Candidate substances that negatively modulate the GA action are for example inhibitors of GA decreasing the rate of, or preventing GA binding to its receptor or compounds desensitizing the receptor. In one preferred embodiment, the assay is designed to identify GA analogs that trigger conformational change in absence of any partner molecules (such as a protein) and also molecules that act as inhibitors of such a conformational change and therefore impede GA action.

The term "GA receptor" as used herein refers to a soluble or membrane-bound molecule to which an active GA binds and activates or inhibits the receptor's associated signaling pathway. Thereby GA binding changes the conformation (three-dimensional shape) of the receptor molecule, leading in turn to a cellular response mediated by the associated signaling pathway. Preferred, in accordance with the present invention, are GA receptors of the GID1 (GIBBERELLIN INSENSITIVE DWARF1) family comprising among others those encoded by wheat (*Triticum aestivum*) GID1 genes (TaGID1-a1, TaGID1-b1 and TaGID1-d1), rice (*Oryza sativa*) GID1 gene (OsGID1), cotton GID1 genes (GhGID1-1 to GhGID1-6) and *Arabidopsis thaliana* GID1 genes (AtGID1a, AtGID1b, and AtGID1c). Especially preferred are the proteins *Arabidopsis* GID1B, its mutant version GID1B.5, and GID1C, as contained in sensors having sequence SEQ ID No.2, SEQ ID No.13 or SEQ ID No.26, respectively.

In one embodiment of the invention, the assay is used in a heterologous system, which here means 'between species' or 'from one species to another'. Thus, the GA receptor being part of the sensor peptide can be derived from an organism different from the organism (preferably microorganism) used for the assay. Thereby it is preferred to use a microorganism without endogenous GAs. For example, a sensor peptide comprising a GA receptor having the sequence of an *Arabidopsis thaliana* GA receptor is used for an assay in yeast such as *Saccharomyces cerevisiae* or in bacteria such as *Escherichia coli.*

It is in particular preferred that the GA receptor portion of the sensor peptide according to the invention is derived from *Arabidopsis thaliana* GID1B (NCBI database ACCESSION Q9LYC1; VERSION Q9LYC1.1 GI:75335642), since it showed the highest specificity for bioactive GAs in in vitro assays and in assays carried out in yeast. Furthermore, it is preferred that the GA receptor portion of the sensor peptide according to the invention is derived from *Arabidopsis thaliana* GID1C (NCBI database ACCESSION Q940G6 VERSION Q940G6.1 GI:75331827) since it showed the highest specificity for bioactive GAs in in planta assays. Furthermore, the present invention provides preferably methods according to the invention wherein the sensor peptide used for a first in vitro screen or a screen carried out in microorganisms, especially in yeast, of candidate substances, such as components of a compound library, is based on GID1B, preferably having at least 80% identity to SEQ ID No. 2, and a validation of hits resulting from that first screening in planta uses a sensor peptide based on GID1C, preferably having at least 80% identity to SEQ ID No. 13.

The present invention provides further methods for identifying substances that modulate GA action through targeting its receptor or acting as a GA functional analog, wherein the sensor peptide has at least 80% identity to SEQ ID No. 2 or to SEQ ID No. 13. Needless to say, that a sensor peptide having at least 80% identity to SEQ ID No. 2 or to SEQ ID No. 13 should be able to bind GA and to restore bioluminescence after conformational change, hence, has the overlap as defined above.

The term "sensor peptide" as used herein refers to a peptide that has been specifically designed to be a biosensor able to detect conformational change of a GA receptor triggered by binding of GA or a functionally analogous molecule.

Thereby the sensor peptide of the invention relies on the ability of the GA receptor, such as GID1, to change its conformation upon GA binding. This change in the conformation is detected in the method of the present invention using split-protein reassembly (also called protein-fragment complementation) of a bioluminescent reporter, such as luciferase, or a fluorescent protein. The individually non-functional fragments of the reporter or the luciferase peptide are induced to reassemble and the reassembled fragments produce an enzymatic or optical readout. Thus, preferred are methods according to the invention, wherein the luciferase or fluorescent activity of the sensor peptide is indicative of binding and activity of the candidate substance to the sensor.

Preferably, the sensor peptide of the invention (also called herein GA sensor) encompasses first the C-terminal domain of the firefly luciferase, preferably 153 amino acids from amino acid 397 to 550, which is separated from a GID1 receptor moiety, preferably from GID1B or GID1C, by a flexible amino acid linker. The GID1 receptor, preferably GID1B, sequence lacking the first methionine and the stop codon is followed by another linker. Both linkers independently of each other consist preferably of 5-10 amino acids, preferably of 6-8 amino acids and most preferably of 7 amino acids. These amino acids are preferably selected from the group of glycine, alanine, and valine. It is particularly preferred that the linkers consist of 7 glycines. The N-terminal domain of the sensor peptide encompasses the N-terminal domain of the firefly luciferase, particularly preferred the first 416 amino acids from firefly luciferase (amino acids 1-416). It is preferred that the N- and C-terminal firefly luciferase domains in the peptide have an overlap of 10-30 amino acids, more preferably of 15-25 amino acids, even more preferably of 17-21 amino acids and particularly preferred of 19 amino acids, and most preferably of the amino acids 397-416 of the firefly luciferase. Such an overlap seems to be necessary for the luciferase activity once reconstituted as a result of both parts having come into close proximity. The use of non-overlapping fragments failed to report luciferase activity in any of the tests performed by the inventors (see FIG. 7).

Therefore the present invention provides preferably methods for identifying substances that modulate GA action through targeting its receptor, such as GID1, or acting as a GA functional analog comprising the following steps:

a) providing a candidate substance to be tested,
b) providing a sensor peptide,
c) bringing the candidate substance into contact with the sensor peptide,
d) providing conditions sufficient to allow the candidate substance to bind to the sensor peptide,
e) determining whether the candidate substance binds to the sensor peptide, wherein the sensor is a peptide encompassing at its N-terminus a sequence that is at least 90% identical with amino acids 397-550 of the firefly luciferase according to SEQ ID No. 1 followed by a first linker, a sequence that is at least 90% identical with a GA receptor of GID1 family, a second linker and at its C-terminus a sequence that is at least 90% identical with amino acids 1-416 of the firefly luciferase according to SEQ ID No. 1 and wherein the C-terminal and N-terminal sequences of firefly luciferase have an overlap of 10-30 amino acids.

Optionally, said method comprises further the following steps:

f) adding a substance known to bind the sensor peptide such as a natural ligand of the used GA receptor, such as $GA_3$ or $GA_4$ for GID1, and providing conditions sufficient to allow binding of the substance known to bind the sensor peptide, and
g) determining whether the candidate substance is able to compete with the substance of step f) for binding to the sensor peptide.

Thereby step g) may also be part of step e) of the inventive method, when the substance known to bind the sensor peptide is allowed to bind to the sensor peptide before step e) and preferably before step c) takes place.

Furthermore the present invention refers to a sensor peptide specifically designed for carrying out the methods according to the invention. This particularly well suited sensor peptide is represented by SEQ ID No. 2 and encompasses first 153 amino acids from the C-terminal domain of the firefly luciferase (397-550), which is separated from the GID1B sequence by a seven-glycine ($Gly_7$) linker, thereby the GID1B sequence lacks the first methionine and the stop codon and is followed by another seven-glycine ($Gly_7$) linker. The C-terminal domain of the sensor encompasses the first 416 amino acids from firefly luciferase (1-416).

In addition the sensor peptide represented by SEQ ID No. 13 is also adapted to be especially suited for a method according to the invention. It encompasses first 153 amino acids from the C-terminal domain of the firefly luciferase (397-550), which is separated from the GID1C sequence by a seven-glycine ($Gly_7$) linker, thereby the GID1C sequence lacks the first methionine and the stop codon and is followed by another seven-glycine ($Gly_7$) linker. The C-terminal domain of the sensor encompasses the first 416 amino acids from firefly luciferase (1-416).

A sensor peptide according to the invention has at least 80% identity, preferred 85% identity, more preferred 90% identity, even more preferred 95% identity and particularly preferred 98% identity with SEQ ID No, 2 or to SEQ ID No. 13 and/or has preferably the same functionality as SEQ ID No. 2 or SEQ ID No. 13, respectively. Having the same functionality means that the sensor peptide comprises at least a part acting as a GA receptor, preferably of the GID1 family, and at its N-terminus and at its C-terminus each an inactive fragment of a bioluminescent or fluorescent reporter protein that together have significant bioluminescent or fluorescent activity through complementation after conformational change of the GA receptor.

The term "sequence identity", as used herein, indicates the percentage match of sequences by using an alignment between two sequences. An alignment is simply a correspondence between the sequences, in which each character in a sequence is assigned no more than one (maybe none) of the symbols in the sequence is maintained, but in which gaps might be introduced into one or both sequence(s) to maximize identity. The sequence identity is usually an also in regard to the present invention calculated as the total number of matches (identical characters in both sequences at a certain position of the alignment) divided by the total length of the alignment of the two sequences and finally multiplied by 100. "Total length of the alignment", does thereby not refer to the length of the overlap between two aligned sequences, but to the entire length spanned by the aligned sequences, i.e. two sequences of 100 amino acids each, having an identical series of amino acids only in the last 10 amino acids of the first sequence and the first 10 amino acids of the second sequence, would result in a total alignment having a total length of 190 amino acids. Thus "sequence identity" is usually expressed as the percentage (%) of matches (identical characters) in positions from an alignment of two molecular sequences. The above concept can be used to determine the sequence identity of two polypeptide sequences (i.e. amino acid sequences) as well as of two nucleotide sequences (i.e. DNA or RNA). Sequences can be aligned with the use of a variety of computer programs known in the art, as for example BioEdit (Hall, T. A. (1999), *Nucl. Acids. Symp. Ser.* 41, 95-98). Two suitable algorithms for aligning pairs of sequences are the Needleman-Wunsch algorithm and the Smith-Waterman algorithm. Popular tool for pair wise sequence alignment is BLAST.

The term "peptide having at least 80% sequence identity with" as used herein refers to peptides having a sequence that shares at least 80% of their amino acids with the sequence represented by SEQ ID No. 2 or SEQ ID No. 13, respectively, wherein the functionality is maintained. The term "peptide having at least 80% sequence identity with the sequence represented by SEQ ID No. 2 or SEQ ID No. 13" as used herein refers to peptides sharing at least 80% of their amino acids with the element of these sequences representing the GA receptor as well as for the elements of these sequences representing the inactive fragments of the bioluminescent or fluorescent reporter protein that yield significant recovered activity through complementation after conformational change of the GA receptor (preferably a GID1 receptor). In regard to the present invention it is preferred that an inventive sensor peptide based on *Arabidopsis thaliana* GID1B comprises unaltered amino acid residues 49-51 of SEQ ID No. 2. Furthermore, it is preferred that the variation in a "peptide having at least 80% sequence identity" is mainly in non-conserved sequences. Thereby conserved sequences are similar or identical sequences that occur within nucleic acid sequences or protein sequences across species (orthologous sequences) or within the different molecules produced by the same organism (paralogous sequences), because, in general, highly conserved sequences are thought to have functional value.

Thus, the present invention refers to a sensor peptide having at its N-terminus a C-terminal domain of a bioluminescent reporter (preferably firefly luciferase) or a functional homolog having at least 80% identity to that C-terminal domain of the bioluminescent reporter followed by a first linker.

a GA receptor, or a functional homolog having at least 80% identity to a GA receptor, preferably to a GID1 receptor a second linker and at its C-terminus a N-terminal domain of the bioluminescent reporter or a functional homolog having at least 80% identity to that N-terminal domain of the bioluminescent reporter and wherein the N- and C-terminal domains of the bioluminescent reporter in the peptide have an overlap of 10-30 amino acids, wherein the entire sequence of the sensor peptide has at least 80% identity with SEQ ID No. 2 or with SEQ ID No. 13 and wherein the N- and C-terminal domains of the bioluminescent reporter in the peptide have an overlap of 10-30 amino acids.

The present invention refers also to a nucleic acid molecule that encodes a sensor peptide as defined in the sentence before.

The term "sequence that is at least 90% identical with amino acids 397-550 of the firefly luciferase according to SEQ ID No. 1" as used herein refers to peptides comprising a sequence that shares at least 90% of their amino acids with the sequence represented by amino acids 397-550 of SEQ ID No. 1, wherein the overlap of the luciferase remains as defined before. The same applies in an analogous manner to the other percentages and peptides or sequences mentioned. The same definition applies to DNA and especially codon-optimized DNA.

One further aspect of the invention refers to a nucleic acid molecule that encodes a sensor peptide having at least 80% identity with SEQ ID No. 2 or SEQ ID No. 13 wherein the functionality of the sensor peptide remains. Functionality comprises thereby the ability for conformational change upon GA binding and further the ability to restore bioluminescence as response to said binding. SEQ ID No. 2, SEQ ID No. 26 and SEQ ID No. 13 represent thereby each a preferred sensor peptide. Thereby the term nucleic acid refers to each nucleic acid such as DNA, RNA or mRNA encoding a sensor peptide having at least 80% identity with SEQ ID No. 2 or SEQ ID No. 13 and having the functionality of a sensor peptide according to the invention.

Another aspect of the invention is a nucleic acid molecule having a sequence having at least 80% identity, preferred 85% identity, more preferred 90% identity, even more preferred 95% identity and particularly preferred 98% identity with SEQ ID No. 3 or SEQ ID No. 12 encoding a functional sensor peptide of the present invention.

One aspect of the present invention refers to methods for identifying substances that modulate GA action through targeting its receptor, respectively a GID1 receptor, or acting as a GA functional analog carried out as an in vitro assay. These in vitro assays are particularly suitable for the design of high throughput assays that allow the in vitro analysis of potential compounds that modulate GA action or acting as a GA functional analog based on the binding to its receptor. These in vitro assays are conducted using a sensor peptide that has been isolated from plant or animal cells or microorganisms.

Preferred are methods according to the invention being an in vitro assay, wherein step c) comprises forming a reaction mixture comprising at least the candidate substance, the sensor peptide and optionally its substrate luciferin.

Step c) of the inventive method could also be defined as mixing the sensor peptide with the candidate substance. Step c) as well as the complete method of the invention could be performed in solution. This means that the sensor peptide and the candidate substance may be dissolved together in one solution or that a solution of the sensor peptide is mixed with a solution of candidate substance. Such a solution could be based on any suitable solvent as well as buffer solutions or a mixture of a solvent, especially an organic solvent and a buffer. Preferably the candidate substance or a solution of the candidate substance is added to the sensor peptide. A solvent for the candidate substance should not interfere with a component of the inventive method. Denaturation of the sensor peptide should be avoided, too. Hence denaturants, surfactants or other amphiphilic molecules in the reaction mixture should be avoided. A reaction mixture of the inventive method has to include at least both components, a sensor peptide and a candidate substance. Furthermore there may be included a substrate for the bioluminescent reporter, such as D-Luciferin ($LH_2$), a Cofactor such as ATP, a solvent or mixture of different solvents, a buffer system or optionally further additives such as protease inhibitors.

Preferably the candidate substance is in solid form or a solution of the candidate substance is added. Thereby it is preferred that different concentrations of the candidate substance will be added in a way that a concentration series is formed.

The evaluation of a concentration series may allow calculating the affinity of the candidate substance for binding to the sensor peptide. Depending on the binding affinity it may be useful to determine an optimal concentration range for the assay in advance. One embodiment of the present invention refers to a method comprising step c) wherein different concentrations of the candidate substance are added to the sensor peptide (each concentration to one sample containing sensor peptide) which allows a quantitative determination of the binding of the candidate substance after data analysis. $IC_{50}$ and $K_i$ values for candidate substances that inhibit GA can be determined, too.

Preferred are methods of the invention, wherein step d) comprises incubating the reaction mixture under conditions sufficient to allow the candidate substance to bind the sensor peptide, in case the candidate substance is able to bind the sensor peptide.

This means that the reaction mixture is incubated for some time, preferably between 2 minutes and 24 hours, more preferred between 10 minutes and 16 hours, further preferred between 30 minutes and 8 hours and most preferred between 1 hour and 4 hours. The term “suitable conditions” refers mostly to a suitable temperature, which should not be higher than 50° C., preferably at room temperature, and a suitable solvent or buffer used in the reaction mixture. Suitable solvents or buffer solutions should not react with one of the components of the inventive method (assay) and should not precipitate. Furthermore a suitable reaction mixture should not have own bioluminescence. Suitable are reaction mixtures on basis of PBS (phosphate buffered saline)-buffers as well as Tris- and triethanolamine buffers. It is preferred that the pH-value of the used buffer is higher than the isoelectric point of the used sensor peptide. Therefore it is preferred that the used buffer has a pH ≥5.0. Suitable buffers should not contain or only contain minor amounts of bioluminescence quenching substances such as DMSO, iodine ions, and glycine. Besides buffer solutions also common growth media or culture media for cells and microorganism, such as yeast, are suitable.

The present invention refers further to in vitro assays for identifying substances that modulate GA action through targeting its receptor or acting as a GA functional analog, wherein step c) comprises producing a cell extract from a host cell able to produce the sensor peptide.

Producing a cell extract comprises lysis of the host cell able to produce the sensor peptide as a first step and extraction of cellular contents. Cell lysis may be performed using common protocols established for most cell types and organisms, such as methods based on physical disruption of the cell (sonification, freeze-thaw cycles) or detergent-based lysis methods.

In regard to the present invention crude cell extracts (crude cell lysate), a subtraction of a cell lysate such as soluble fractions, or a solution resulting from total protein extraction or purified sensor peptide can be used. The DNA constructs, respectively vectors coding for the sensor peptide are going to be transfected or transformed to the cells or organism by conventional methods.

As used herein a crude cell extract results from disruption of cells and removing of removal of cellular debris generated by cell lysis. The extract will contain a complex mixture of all proteins from the cell cytoplasm, and some additional macromolecules, cofactors and nutrients.

Thereby it is preferred to use a cell lysate resulting from lysed cells that have been ultracentrifuged to remove insoluble matter such as membrane fragments, vesicles, and nuclei, and consisting mostly of cytosol or to use a purified sensor peptide. In fact, it depends on the problem to be solved by the assay whether an in vitro assay based on purified sensor peptide or on crude cell extract is preferred.

A total protein extraction may be resulting from common protocols established for most cell types and organisms isolating nearly all proteins. A purified sensor peptide can be obtained using each commonly known protocol of protein purification intended to isolate a single type of protein from a complex mixture, such as purification of a tagged peptide, affinity chromatography, or immunoaffinity chromatography. For nearly all cell types and organisms optimized protocols for cell lysis and protein purification have been published (e.g. Methods in Molecular Biology, Volume 244, Protein Purification Protocols, $2^{nd}$ edition, 2004, Humana Press).

The present invention refers further to in vitro assays for identifying substances that modulate GA action through targeting a GID1 receptor or acting as a GA functional analog, wherein step d) comprises incubating the cell extract with the candidate substance under conditions sufficient to allow the candidate substance to bind the sensor peptide, in case the candidate substance is able to bind the sensor peptide. Thereby the conditions sufficient to allow the candidate substance to bind the sensor peptide are the same as defined above.

Another aspect of the present invention for identifying substances that modulate GA action through targeting its receptor or acting as a GA functional analog refers to in vivo assays.

The present invention refers further to in vivo assays for identifying substances that modulate GA action through targeting its receptor or acting as a GA functional analog, wherein step c) comprises transforming or transfecting a host cell or an organism with a nucleic acid coding for the sensor peptide. Transformation means thereby the genetic alteration of a cell resulting from the direct uptake, incorporation and expression of at least one nucleic acid sequence coding for a sensor peptide of the present invention. The term “transformation” refers to the introduction of at least one nucleic acid sequence coding for a sensor peptide of the present invention into bacterial cells, plant cells and yeast whereas insertion of the at least one nucleic acid sequence coding for a sensor peptide of the present invention into an animal cell is called transfection. Transformation as well as transfection may be performed using common protocols established for most cell types and organisms, such as *agrobacterium* mediated plant transformation, gene guns, electroporation, chemical-based transfection, or magnetic beads assisted transfection. The present invention refers to methods to identify new GA functional analogs that trigger conformational change of a GA receptor, such as GID1, or of molecules that inhibit such a conformational change. Gibberellins (GAs) are phytohormones essential for many processes in plants. Thus, it is reasonable to perform the in vivo assay in plants or using microorganisms, such as yeast or bacteria, which are transformed easily. To clarify only, it does not refer to methods for treatment or therapy of the human or animal body and also not to diagnostic methods practiced on the human or animal body. Animals including humans do not have GA or its receptor, therefore methods for treatment or therapy of the human or animal body and also diagnostic methods for human or veterinary medicine involving GA are meaningless.

For the expression of the corresponding peptide sensor the nucleic acid sequences coding for a sensor peptide such as the nucleic acids of the present invention can be inserted into expression vectors, such as recombinant bacteriophage, plasmid, or cosmid DNA expression vectors. Therefore, the present invention refers also to nucleic acid molecules containing one of the nucleic acids mentioned above, such as expression vectors. This expression vectors could also encode for fusion polypeptides of the respective sensor peptide and a tag suitable for isolation of the sensor peptide, such as ($His_6$)-Tag. Such tag could be cleavable using a protease cleavage site between the sensor peptide and the tag.

In a preferred embodiment there is an expression control component included in these DNA constructs in order to detect easily whether the transfection was successful and to which extent. Suitable gene transcription markers include, among others, genes for LacZ-β-galactosidases, antibiotic resistant β-lactamases, yeast markers, TetR (tetracycline resistance), KanR (kanamycin resistance), CmR (chloramphenicol resistance), aadaR (spectinomycin resistance), araBAD (arabinose), UR.43, and PLV. In another preferred embodiment these nucleic acids are going to be expressed under the control of a suitable promoter gene sequence. For example, the cytomegalovirus (CMV) promoter is one of the most commonly used promoters for expression of transgenes in mammalian cells. Suitable promoter systems for yeast include for example constitutive, moderate-strength yeast alcohol dehydrogenase (ADH1) promoter.

Furthermore, the expression vectors may contain genetic elements that might affect the subcellular localization of the sensor peptide; for example, the nuclear localization signal (NLS) of the SV40 large T antigen efficiently induces nuclear targeting of proteins.

In regard to the in vivo assays of the invention step c) of the inventive methods bringing the candidate substance into contact with the sensor peptide involves introducing the candidate substance into host cells or an organism. This can be done by conventional methods and depends on one side from the host cell or organism selected and on the other side from the characteristics of the candidate substance.

Some substances permeate through cell membranes or at least some cell membranes because of their chemical structure. Such candidate substances can easily be contacted with the sensor peptide by incubation or simply mixing the candidate substance to the culture medium of the host cell. Otherwise, it can be necessary to add further compounds that mediate uptake of the candidate substance by the host cell or an organism, such as liposomes or magnetic beads.

Other substances are transported across cell membranes or at least some cell membranes by transport proteins in the cell membrane. Such candidate substances can also be contacted with the sensor peptide by adding the candidate substance to the culture medium of the host cell or the organism.

In a further preferred embodiment of the in viva assays according to the invention the candidate substance is an intracellular peptidic compound. Such an intracellular peptidic compound can be selected from any protein or peptide expressed physiologically or after transfection inside the cells to be tested, or physiological or artificial derivatives of peptides and proteins such as lipoproteins, glycoproteins, glycopeptides, peptides or proteins with secondarily modified amino acids, peptides or proteins with protecting groups, quaternary structures of proteins, and compounds containing an amino acid chain of at least two amino acids.

A DNA molecule, RNA molecule, siRNA molecule, miRNA molecule, or a precursor thereof, can be introduced into cells or organisms by transformation or transfection using protocols known to a person skilled in the art and being adapted to the host cell or organism.

Therefore, one aspect of the present invention are in vivo assays for identifying substances that modulate GA action through targeting its receptor or acting as a GA functional analog, wherein step c) further comprises transforming or transfecting a host cell with a nucleic acid coding for the candidate substance or incubating the host cell with the candidate substance.

Suitable host cells may be selected from the group comprising or consisting of a plant cell, a fungal cell, and a bacterial cell. The in vivo methods comprise that at least a sensor peptide and a candidate substance come into contact inside of a host cell in presence of a substrate for the bioluminescent reporter.

The present invention relates furthermore to cells of the strain AH109 of the species *Saccharomyces cerevisiae* expressing the sensor peptide according to SEQ ID No. 2 deposited at the German Collection of Microorganisms and Cell Cultures with deposit number 28095. This strain has been produced as described in examples 1 and 2 and is especially adapted to suit the methods according to the invention.

The in vivo methods of the present invention for identifying substances that modulate GA action through targeting its receptor or acting as a GA functional analog are suitable for determining the localization of active forms of GA over time, for example during development of a cell or an organism or under different conditions of living cells. For such studies it is important that the sensor peptide, respectively, the method according to the invention has a suitable dynamic spatial-temporal resolution.

There are 61 different natural amino acid codons but only 20 different translated unmodified natural amino acids that are incorporated in proteins. The overabundance in the number of codons allows many amino acids to be encoded by more than one codon. There are differences in the frequency of occurrence of synonymous codons in coding DNA of plants, bacteria and animals, which may cause a plant gene to be poorly expressed in other organisms, including yeast. This can be overcome by in silico reverse translation of the amino acid sequence of the encoded protein using codons preferred by the target organism such as yeast. An appropriate DNA sequence can then be synthesized specifically to efficiently express the plant gene in the host organism. However, it has been found that it is advantageous that the nucleic acid sequence coding for the sensor peptide in the strain having Accession number 28095 (deposited at DSMZ—German Collection of Microorganisms and Cell Cultures) has not been codon optimized for yeast.

Within the in vivo methods of the present invention used as screening assay it is preferred to use a DNA sequence coding for the sensor peptide that has not been optimized according to the codon usage of the host cell. This improves the dynamic spatial-temporal resolution. One advantage for high throughput screening assays, performed preferably in yeast, regarding non-optimized codon composition is the slower protein production and maturation which allows a delay in starting to detect the conformational change and therefore readout of the assay.

The aim of the methods according to the present invention is to find candidate substances having at least one biological or pharmaceutical effect of GA or, respectively, modulating the effect of GA binding to its receptor, including competitive antagonists of GA. Depended of the subject-matter of the study it can be useful to provide and contact not only the candidate substance to be tested and the sensor peptide but also GA, a GA derivative, a co-factor, or a DELLA protein. Within in vivo methods according to the invention it can be that GA or a GA derivative is present as endogenous substance in the host cell. Alternatively, when using a host cell without GA or a GA derivative this can be introduced into the host cell. The GA or the GA derivative can be added either during step c) or during e). The GA or a GA derivative can simply be added to the reaction mixture, in case of the in vitro methods according to the invention.

When adding GA or a GA derivative it is possible to determine whether the candidate substance is able to modulate the action of the GA or the GA derivative or if a candidate substance is able to replace GA or a GA derivative from the binding side of its receptor.

Another embodiment of the present invention relates to a method for identifying substances that modulate GA action through targeting its receptor, namely GID1, or acting as a GA functional analog comprising the following steps:

a) providing a candidate substance to be tested,
b) providing a sensor peptide,
b') providing a GA or a GA derivative,
c) bringing the candidate substance into contact with the sensor peptide and the a GA or the GA derivative,
d) providing conditions sufficient to allow the candidate substance to bind to the sensor peptide, to the GA or to the GA derivative,
e) determining whether the candidate substance affects GA or GA derivative binding to a GA receptor, wherein the sensor is a protein encompassing at its N-terminus a sequence that is at least 90% identical with the amino acids 397-550 of the firefly luciferase according to SEQ ID No. 1 followed by a first linker, a GID1 receptor, a second linker and at its C-terminus a sequence that is at least 90% identical with amino acids 1-416 of the firefly luciferase according to SEQ ID No. 1 and wherein the luciferase activity of the sensor is indicative for the inhibition of the GA or the GA derivative binding by the test substance.

The GA or a GA derivative as used herein is known to bind to the sensor peptide, such as a natural ligand of the used GA receptor, such as $GA_3$ or $GA_4$ for GID1.

Additionally, within the methods according to the invention it is possible to add not only the test substance but also another component that should be analyzed in regard to its influence on the modulation of GA action by the test substance.

Step e) of the methods according to the present invention refers to experimentally determining whether the candidate substance binds to the sensor peptide or, optionally, whether the candidate substance modulates the binding of GA or the GA derivative to a GA receptor, such as GID1.

As described above the sensor peptide of the present invention is based on a bioluminescent reporter, preferably the firefly luciferase fragment complementation strategy. Luciferins are a class of small-molecule substrates that are oxidized in the presence of bioluminescent reporter to produce oxyluciferin and energy in the form of light that can be detected. The firefly luciferase catalyzes the following chemical reaction:

Adenylation of a substrate, such as luciferin, using ATP and

Oxidation of the resulting luciferyl adenylate.

Light is emitted because the reaction forms oxyluciferin in an electronically excited state. Thus, light is emitted when luciferase acts on the appropriate luciferin substrate.

Determining whether the candidate substance binds to the sensor peptide or optionally the candidate substance modulates the GA or the GA derivative binding to a GA receptor may be done by measurement of luminescence of the firefly luciferase wherein occurrence of luminescence indicates functional binding of the candidate substance to the sensor peptide and a change in the luminescence indicates modulation of the GA or the GA derivative binding to a GA receptor. Measurement of luminescence of the firefly luciferase may also be used for determining whether the candidate substance is able to compete with the substance of optional step f) for binding to the sensor peptide, wherein a change in the luminescence indicates competition, in particular, whether the candidate substance was added prior to the substance known to functionally bind to the sensor peptide a decrease in the luminescence indicates competition and whether the substance known to bind the sensor peptide was added prior than the candidate substance an increase in the luminescence indicates competition.

Consequently, step e) and step g) comprise preferably adding a luciferin substrate to the reaction mixture or to the host cell prior to imaging. For measuring luciferase luminescence in living cells optimized luciferin substrates have been developed; these optimized luciferin substrates may be simply added to the culture medium. The total amount of light emitted from bioluminescence is typically small and not detectable by the human eye, but it can normally detected Using a photodetector as part of a luminescence spectrometer or by using a sensitive CCD camera For controls, to ascertain whether the method is properly working in the hands of the experimenter, a negative control sample and a positive reference sample (a sample containing a substance known to inhibit GA action) should always be used together with the candidate substance to be tested. This is a standardized procedure with biologically or diagnostic assays. This means that at the same time or immediately one after the other, not only the candidate substance is tested within the inventive method, but also a negative control sample, which can be a blank and/or a sample containing a substance known not to inhibit GA action. Such a blank would comprise all components, such as the sensor peptide, a GA derivative and optionally buffer, except for the candidate substance.

For example, replacement of the GID1B amino acid residues 49-51 with alanines in the SEQ ID No. 2 rendered a GA sensor peptide insensitive, which was then used as control in different assays (GID1.9B).

Often, but not always, these ingredients are provided in already prepared solutions ready- or close to ready-for-use. There may be also combinations of different ingredients already added together. A further advantage is that such kits have been independently quality controlled. Therefore, kits are a very popular tool in laboratories in research, diagnostics and industry.

The following components can be included in such kits being one aspect of the invention:

a) a sensor peptide or a nucleotide molecule coding for the sensor peptide and/or a host organism comprising a nucleotide molecule coding for the sensor peptide,
b) GA or a derivative thereof which may be used as a reference sample,
c) buffer solution, and/or
d) wash solution.

DESCRIPTION OF THE FIGURES

Shown is the luciferase intensity over time as a measure of binding with increasing concentrations of 4 different GA isoforms ($GA_1$, $GA_3$, $GA_4$ and the biologically inactive $GA_4$-methyl ester ($GA_{4Mees}$)) to the sensor peptide

Shown is the luciferase intensity over time as a measure of binding with increasing concentrations of 4 different GA isoforms ($GA_1$, $GA_3$, $GA_4$ and the biologically inactive $GA_4$-methyl ester ($GA_{4Me}$)) to the GID1B based sensor peptide with (B) or without (A) co-expression of a DELLA protein (GAI), or to the GID1C based sensor peptide with (D) or without (C) co-expression of a DELLA protein (GAD.

Figure 7:
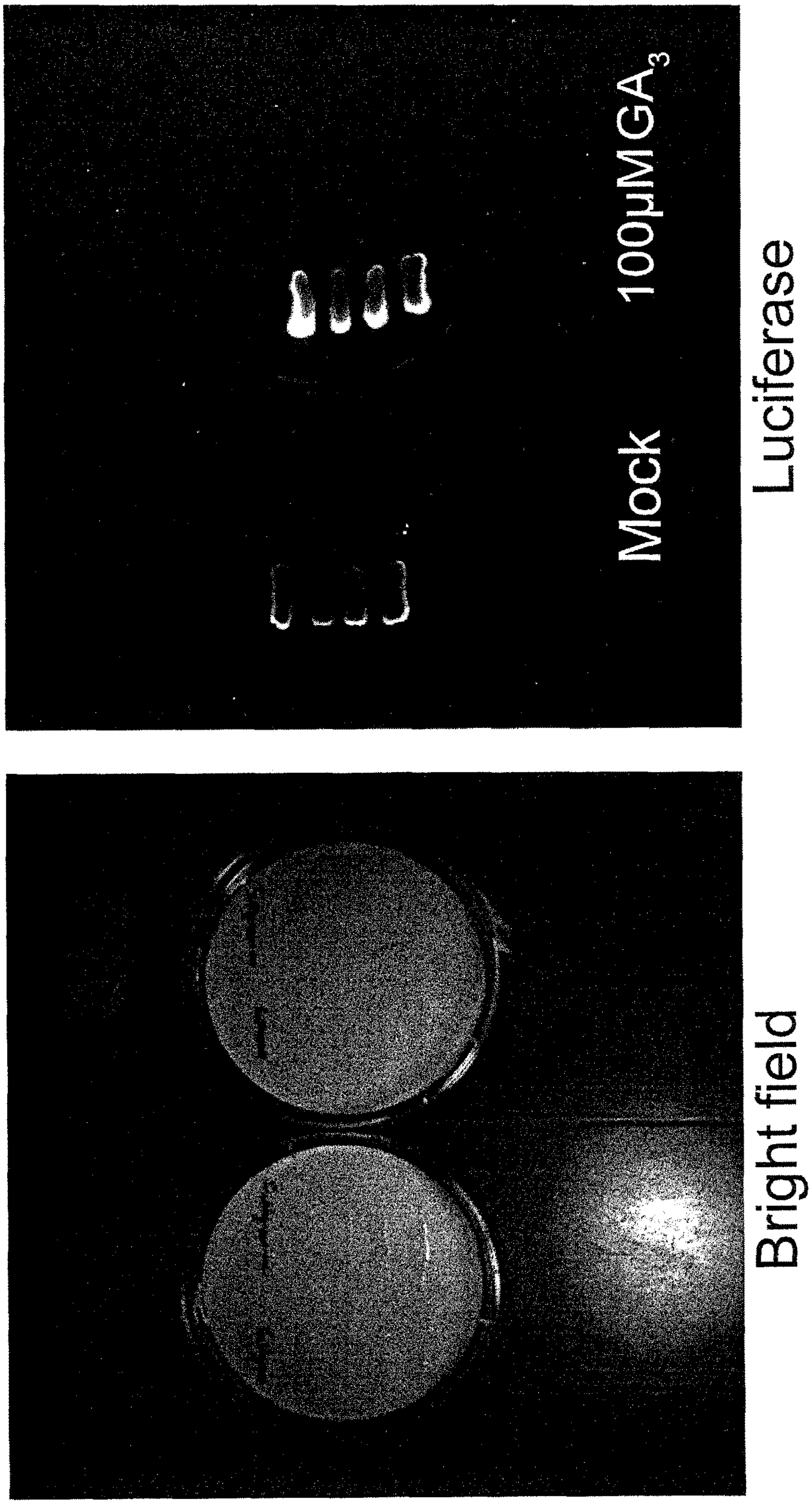

FIG. 7: shows a comparison of sensor peptides based on *Arabidopsis thaliana* GID1B flanked with overlapping (left row on each plate) and non-overlapping (right row on each plate) fragments of firefly luciferase. 4 yeast colonies were each incubated in presence of Mock (left plate) or 100 μM GA3 (right plate).

Figure 8:
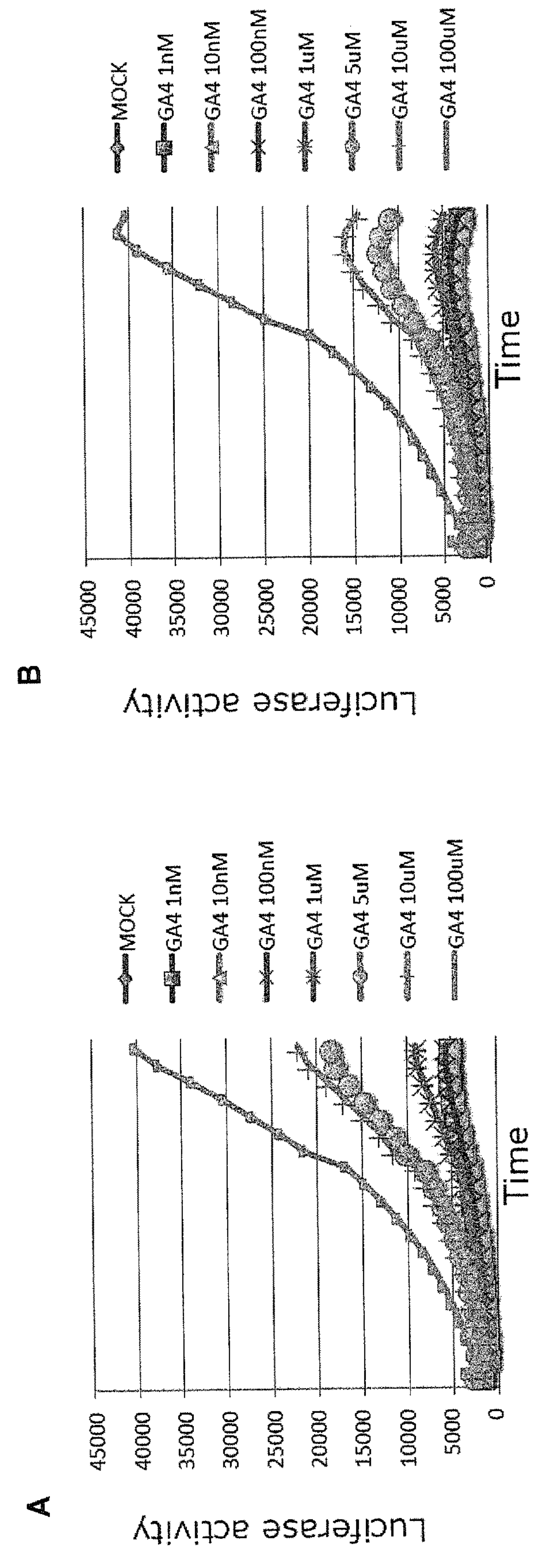

FIG. 8: shows a comparison of the sensitivity of *Arabidopsis thaliana* GID1B (panel A) and *Arabidopsis thaliana* GID1B.5 (having mutation V53A; panel B) based sensors in *S. cerevisiae.*

EXAMPLES

Example 1: Generation of Plasmids Coding for the Sensor Peptides

*Arabidopsis thaliana* GID1B and GID1C cDNA sequences flanked by two partially overlapping fragments of the firefly luciferase coding sequence and separated by two linkers encoding seven glycines each were combined into a single expression vector. To obtain GID1B and GID1C sequences, total RNA was isolated from inflorescences of 30-day old *Arabidopsis thaliana* plants. cDNA synthesis was carried out using 1 μg RNA that had been treated with RNAse-free DNAse I (Fermentas) following the manufacturer's instructions. The GID1B (At3g63010) coding sequence was amplified by polymerase chain reaction (PCR) using that cDNA as template and primers G-16509 and G-16511 (see Table 1). GID1C (At5g27320) coding sequence was amplified by PCR using that cDNA as template and primers G-16512 and G-16514 (see Table 1). Val 53 was replaced by Ala in GID1B sequence following a two-step point mutation strategy. To that end, two fragments were generated by PCR using the primer pair G-16509 and G-36467 and the primer pair G-36466 and G-16511 (see Table 1). Both overlapping PCR products were combined in a single PCR reaction and amplified using the primers G-16509 and G-16511 to originate a GID1B-based construct named GID1B.5. The obtained PCR products were used by the inventors as template for a second PCR with the primers G-25723 and G-25724 (GID1b and GID1b.5) and G-25728 and G-25729 (GID1c) to add part of the linker sequences. Overlapping parts of firefly luciferase coding sequences, encoding the N- and C-terminal domains were amplified by PCR from a firefly luciferase coding sequence containing plasmid with the primers G-25721, G-25722 (for GID1b and GIID1b.5 containing constructs) or G-25727 (for GID1c containing constructs), G-25725 (for GID1b and GID1b.5 containing constructs) or G-25730 (for GID1c containing constructs), and G-25750 (see Table 1). In order to join the three parts of the sensors (C-LUC, GID1 and N-LUC), 0.5 μl of each of the previous PCR reactions were mixed and another PCR with primers G-25721 and G-25750 (see Table 1) was performed. In order to generate firefly non-overlapping N- and C-terminal domains the inventors followed the same procedure described before using the primer G-25726 instead of G-25750 (see Table 1). The PCR products were isolated, and the ends were A tailed by incubating in a thermocycler 7.8 μl of the PCR product with 0.2 μl of Taq polymerase in the presence of 1 μL of dATP and 1 μL of Taq polymerase buffer for 30 minutes at 72° C. The DNA fragments were then introduced into the pCR8/GW/TOPO® cloning vector (Invitrogen, Life Technologies) using the TOPO® cloning method by overnight room temperature incubation, to generate the plasmids IR202 (GID1B sensor), IR237 (GID1B.5 sensor), IR240 (GID1B.5 sensor with non-overlapping firefly fragments) and IR213 (GID1C sensor).

Plasmids IR202, IR237 and IR213 were digested with Nhel and Miul restriction enzymes and the C-LUC-GID1-N-LUC fragments were introduced by Gateway® LR Clonase™ mediated recombination into two destination vectors: the yeast pDEST22 plasmid (Invitrogen, Life Technologies) and the plant binary plasmid pFK210, generating the plasmids IR206 (GID1BLUC-pDest22), IR238 (GID1B.5LUC-pDEST22), IR241 (GID1B.5LUCnon-overlapping-pDEST22) and 214 (GID1CLUC-pDest22) or IR208 (35S::GID1BLUC), IR239 (35S::GID1B.5LUC) and 216 (353::GID1CLUC).

TABLE 1

Oligonuclectide primers used for generation of recombinant plasmids

| Primer ID | Purpose | Sequence |
|---|---|---|
| G-16509 (SEQ ID No. 4) | GID1b cDNA PCR amplification | ATGGCTGGTGGTAACGAAGTC |

TABLE 1-continued

| Oligonuclectide primers used for generation of recombinant plasmids | | |
|---|---|---|
| Primer ID | Purpose | Sequence |
| G-16511 (SEQ ID No. 5) | GID1b cDNA PCR amplification | CTAAGGAGTAAGAAGCACAG |
| G-16512 (SEQ ID No. 14) | GID1c cDNA PCR amplification | ATGGCTGGAAGTGAAGAAGTTAAT CT |
| G-16514 (SEQ ID No. 15) | GID1c cDNA PCR amplification | TCATTGGCATTCTGCGTTTAC |
| G-25721 (SEQ ID No. 6) | C-terminal domain of firefly luciferase PCR amplification | Atgtccggttatgtaaacaatcc |
| G-25722 (SEQ ID No. 7) | C-terminal domain of firefly luciferase with linker PCR amplification for GID1b | GACTTCGTTACCACCAGCtcctccgcca cccccgccacccacggcgatctttc |
| G-25723 (SEQ ID No. 8) | Addition of linker to GID1b cDNA during PCR amplification | gcggaggaGCTGGTGGTAACGAAGTC |
| G-25724 (SEQ ID No. 9) | Addition of linker to GID1b cDNA during PCR amplification | gcctccaccAGGAGTAAGGCACAG |
| G-25725 (SEQ ID No. 10) | Addition of linker to N-terminal domain of firefly luciferase during PCR amplification for GID1b | CTGTGCTTCTTACTCCTggtggaggcgg aggcggaggcgaagacgccaaaaacataaag |
| G-25727 (SEQ ID No. 16) | Addition of linker to C-terminal domain of firefly luciferase during PCR amplification for GID1c | GATTAACTTCTTCACTTCCAGCtcctc cgccacccccgccacccacggcgatctttc |
| G-25728 (SEQ ID No. 17) | Addition of linker to GID1c cDNA | ggcggaggaGCTGGAAGTGAAGAAGT TAATC |
| G-25729 (SEQ ID No. 18) | Addition of linker to GID1c cDNA during PCR amplification | gcctccaccTTGGCATTCTGCGTTTAC |
| G-25730 (SEQ ID No. 19) | Addition of linker to N-terminal domain of firefly luciferase during PCR amplification for GID1c | GTAAACGCAGAATGCCAAggtggaggc ggaggcggaggcgaagacgccaaaaac |
| G-25750 (SEQ ID No. 11) | N-terminal domain of firefly luciferase during PCR amplification | Ttatccatcttgtcaatc |
| G-25726 (SEQ ID No. 20) | PCR amplification of N-terminal domain of firefly luciferase non-overlapping | TtaaAtcataggaccctcac |
| G-36466 (SEQ ID No. 21) | Introduction of V53A mutation into GID1b by PCR amplification | CCGTAAAgccCCCGCCAACTC |
| G-36467 (SEQ ID No. 22) | Introduction of V53A mutation into GID1b by PCR amplification | GGCGGGgcTTTACGGTAAGGAA C |
| G-26500 (SEQ ID No. 23) | DELLA protein GAI gene PCR amplification, without ATG | AAGAGAGATCATCATCATC |
| G-23313 (SEQ ID No. 24) | DELLA protein GAI gene PCR amplification | ctaattggtggagagtttccaag |

Example 2: Method of the Invention Carried Out in Yeast

Figure 1:
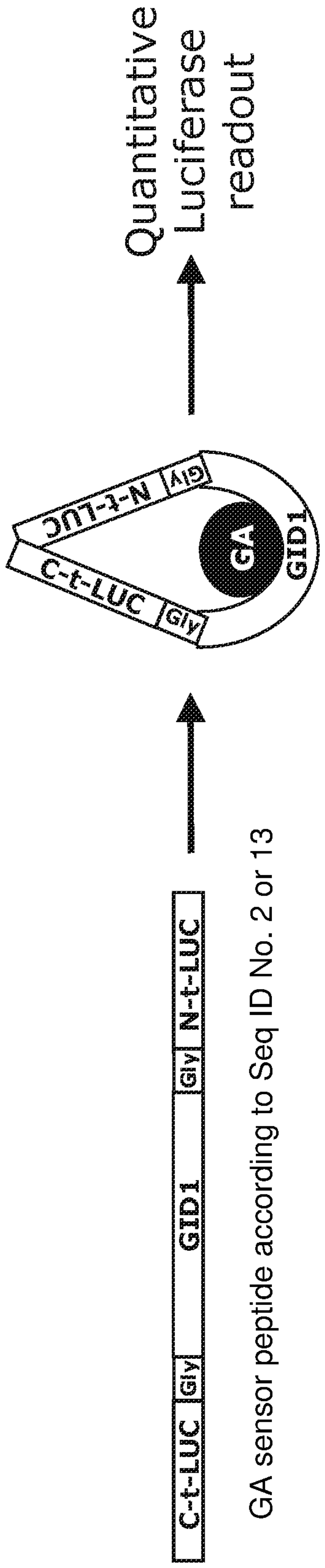
FIG. 1: shows a diagram of the GA sensor (according to Seq ID No. 2 or 13) principle and its design: Binding of GA or an analog thereof to GID1 triggers a conformational change which results in the reconstitution of the luciferase enzymatic activity providing a visible and quantitative read-out of the presence of binding and activity of GA or its analog. N-t-LUC and C-t-LUC stand for the amino- and carboxy-terminal domains of the firefly luciferase protein. "-t" means terminal.
Figure 2:
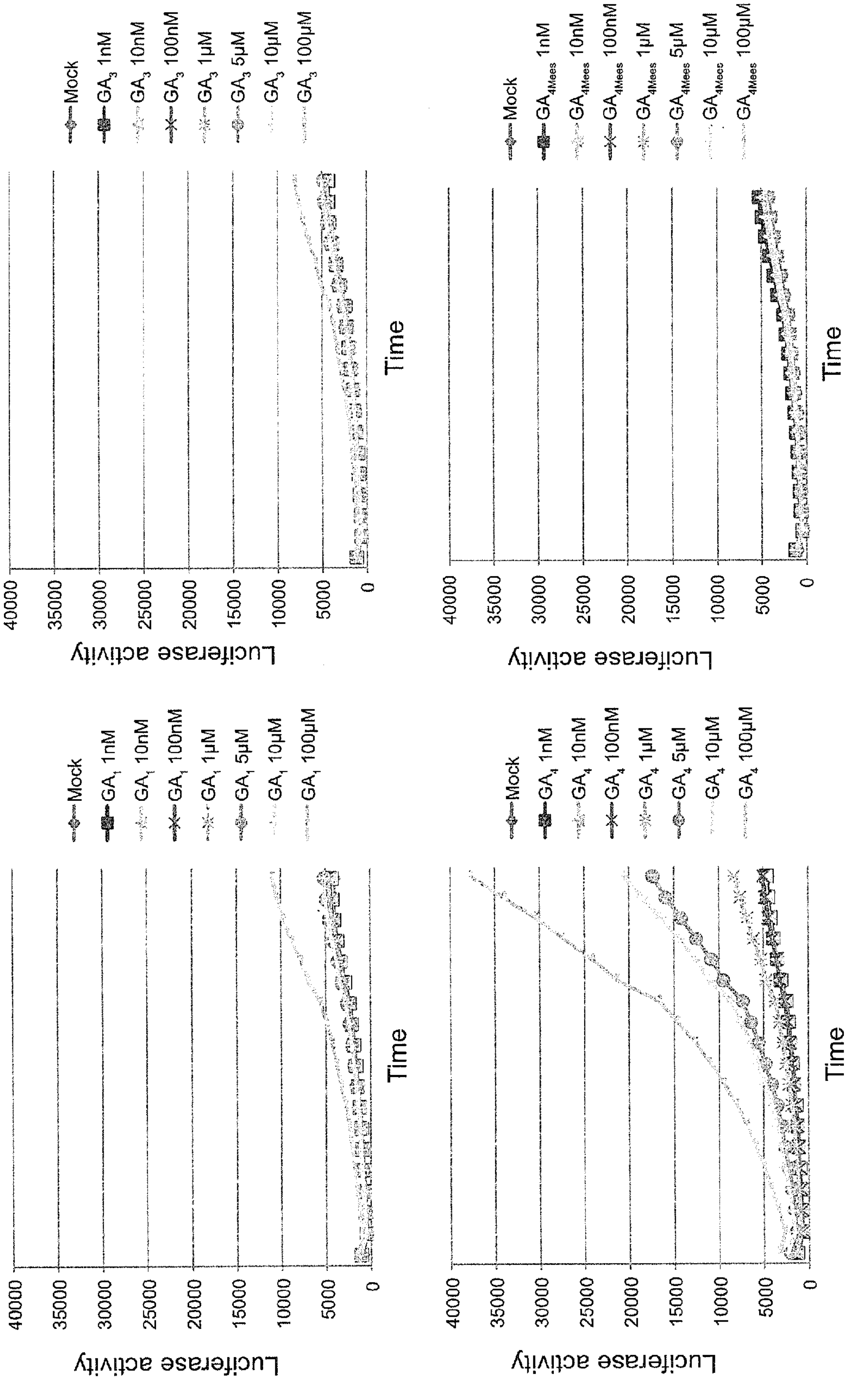
FIG. 2: shows results of the assay performed in *Saccharomyces cerevisiae* using an *Arabidopsis thaliana* GID1B based sensor.
Figure 3:
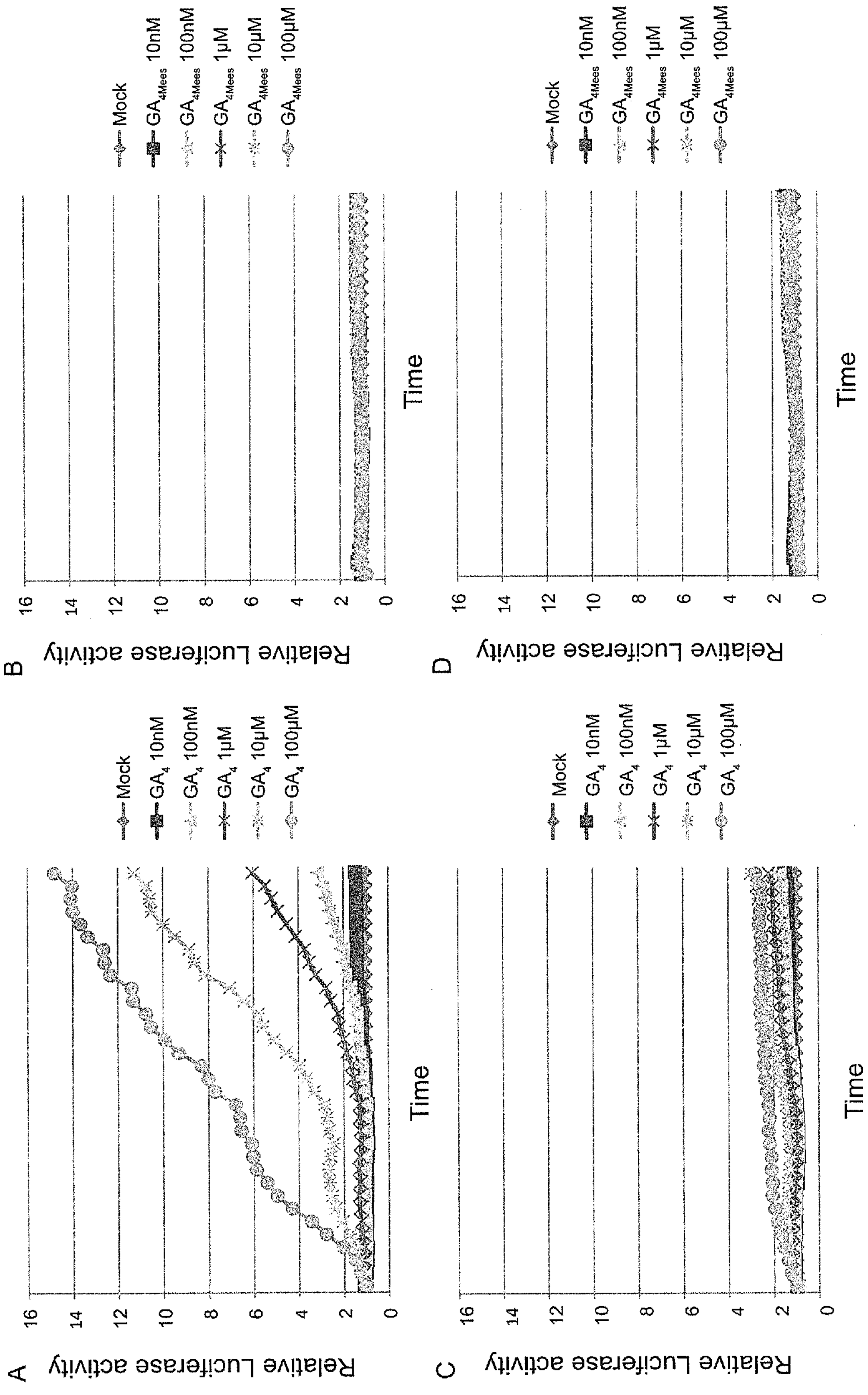
FIG. 3: shows a comparison of the sensitivity of *Arabidopsis thaliana* GID1B (panels A and B) and *Arabidopsis thaliana* GID1C (panels C and D) based sensors in *S. cerevisiae*. Thereby $GA_{4mees}$ means $GA_4$-methyl ester.

In order to assess and quantify the sensitivity of the inventive sensor peptide to increasing concentrations of different GA isoforms, the inventors introduced different sensor peptides in a heterologous system devoid of GA, namely baker yeast cells (*Saccharomyces cerevisiae*). The sensor peptides according to SEQ ID No. 2 and to SEQ ID No. 26, based on *Arabidopsis thaliana* GID1B as receptor and the sensor peptide according to SEQ ID No. 13, based on *Arabidopsis thaliana* GID1C as receptor were tested. Yeast cells bearing the sensor peptides according to the invention were assayed in solid media in the presence/absence of two different concentrations of two GA isoforms with different biological activities, $GA_3$ and $GA_4$ as described below in all cases the inventors found a correlation between luciferase intensity and the concentration and activity of the different concentrations and hormone forms (data not shown). The inventors then performed a quantitative liquid assay on a larger scale. This time the inventors extended the study to increasing concentrations of other GA isoforms with different biological activities. Among these GA isoforms, $GA_4$ has been described as the most biologically active in in planta assay, while $GA_3$ and $GA_1$ showed less activity and $GA_4$-methylester was barely active. GA sensors based on *Arabidopsis thaliana* GID1B as well as based on *Arabidopsis thaliana* GID1C were able to differentially report the presence of different isoforms and concentrations according to their predicted biological activity (see FIGS. 2 and 3). Nevertheless, the *Arabidopsis thaliana* GID1B based vector performed in a more sensitive manner in these assays (FIG. 3). Furthermore, the sensor according to SEQ ID No. 26 having the mutation V53A keeps also ability to report presence of bioactive GAs in yeast assays (see FIG. 8).

The plasmids IR206 and IR214 were introduced into the *Saccharomyces cerevisiae* strain AH109 (Clontech). The inventors deposited the IR206 containing yeast strain at the DSMZ (reference P37913, entry number 28095). For solid assays, 5 colonies were diluted in 100 μL of distilled water and 10 μL were spotted onto two separate Nylon membranes. The membranes were incubated in a Petri dish containing solid selective media (YNB, MPBlo, supplemented with CSM $Trp^-$, Bio 101) and grown at 30° C. for 3 days. Membranes were subsequently transferred to a new dish of selective media supplemented with 1.25 mM of firefly substrate for 4 hours in the dark and at room temperature. Later on, membranes were transferred to plates with selective media and firefly substrate in the presence or absence of $GA_3$ 100 μM. Luciferase activity was recorded using default time-laps settings in a CCD camera device (Hamamatsu).

Two representative colonies were selected and plated onto Nylon membranes as described before. After 3 days at 30° C. the membranes were incubated in selective media containing luciferase substrate for 4 hours in dark at room temperature. Each replicate was subsequently transferred to plates containing 10 and 100 μM of two forms of active GAs, $GA_3$ and $GA_4$. Luciferase activity was recorded as indicated before. For liquid assays, the inventors inoculated one representative colony for each version of the sensor in 5 ml of selective media (YNB, MPBlo, supplemented with CSM $Trp^-$, Bio 101) containing luciferase substrate and grown under shaking at 28° C. for 18 hours. The yeast culture was adjusted to a density of $OD_{500}$=0.6 and 50 μL were placed in each well of a 96 well microtiter plate together with 50 μL of selective media containing luciferase substrate and supplemented with increasing concentrations of 4 different GA isoforms ($GA_1$, $GA_3$, $GA_4$ and $GA_4$-methyl ester). Plates were incubated for 16 hours at 28° C. in a cabinet and luciferase activity was recorded during the entire period of the experiment using a Topcount™ device (Perkin Elmer).

Example 3: Method of the Invention Carried Out as In Planta Assay

To validate in planta the results obtained in yeast, the inventors introduced the GA sensors under the control of the constitutive viral promoter 35S into *Arabidopsis thaliana* plants. The constructs IR208 and IR216 were independently introduced using the floral dip method of *Agrobacterium*-mediated transformation into the *Arabidopsis thaliana* Ler-1 (*Landsberg erecta*) wild-type strain and its isogenic ga1-3 mutant strain (containing a deletion in the gene for the enzyme that catalyzes an early step in the synthesis of GA: Sun et al., Plant Cell, 1992, 4, 119-128). Plants were grown in soil under Basta™ selection and short day conditions (8h light/16h dark).

GA3ox1-GUS and GA3ox2-GUS *Arabidopsis* reporter lines were described in Hua et al., Plant Cell, 2008, 20, 320-336. GA3 oxidase catalyzes consecutive reactions that convert GA intermediates to the bioactive forms. Because GA3 oxidase catalyzes the last step of the synthesis of bioactive GA, the temporal and spatial expression patterns of the encoding GA3ox genes are likely to reflect when and where bioactive GA isoforms are being made in plants.

Figure 4:
FIG. 4: shows activity of an inventive sensor peptide (based on *Arabidopsis thaliana* GID1C) in plants with impaired GA production (ga1-3 mutants). The image was taken 15 minutes after spraying the plants with either mock or $GA_3$ containing solution.
Figure 5:
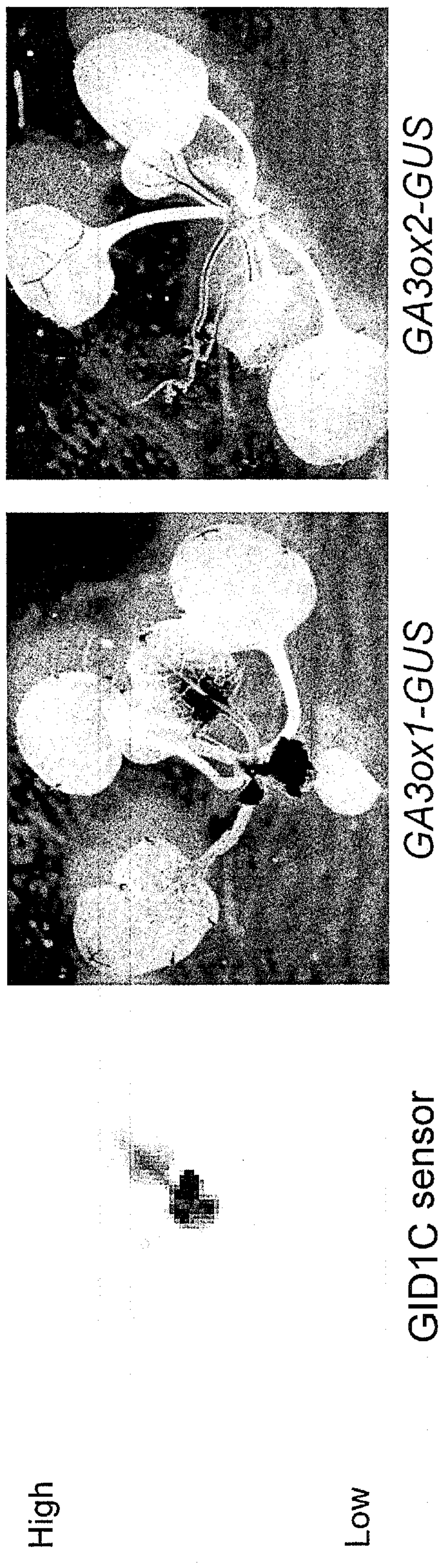
FIG. 5: shows that activity of an inventive sensor peptide (based on GID1C) in plants (background line) matches the expression patterns of two of the main GA biosynthetic enzymes.
Figure 6A:
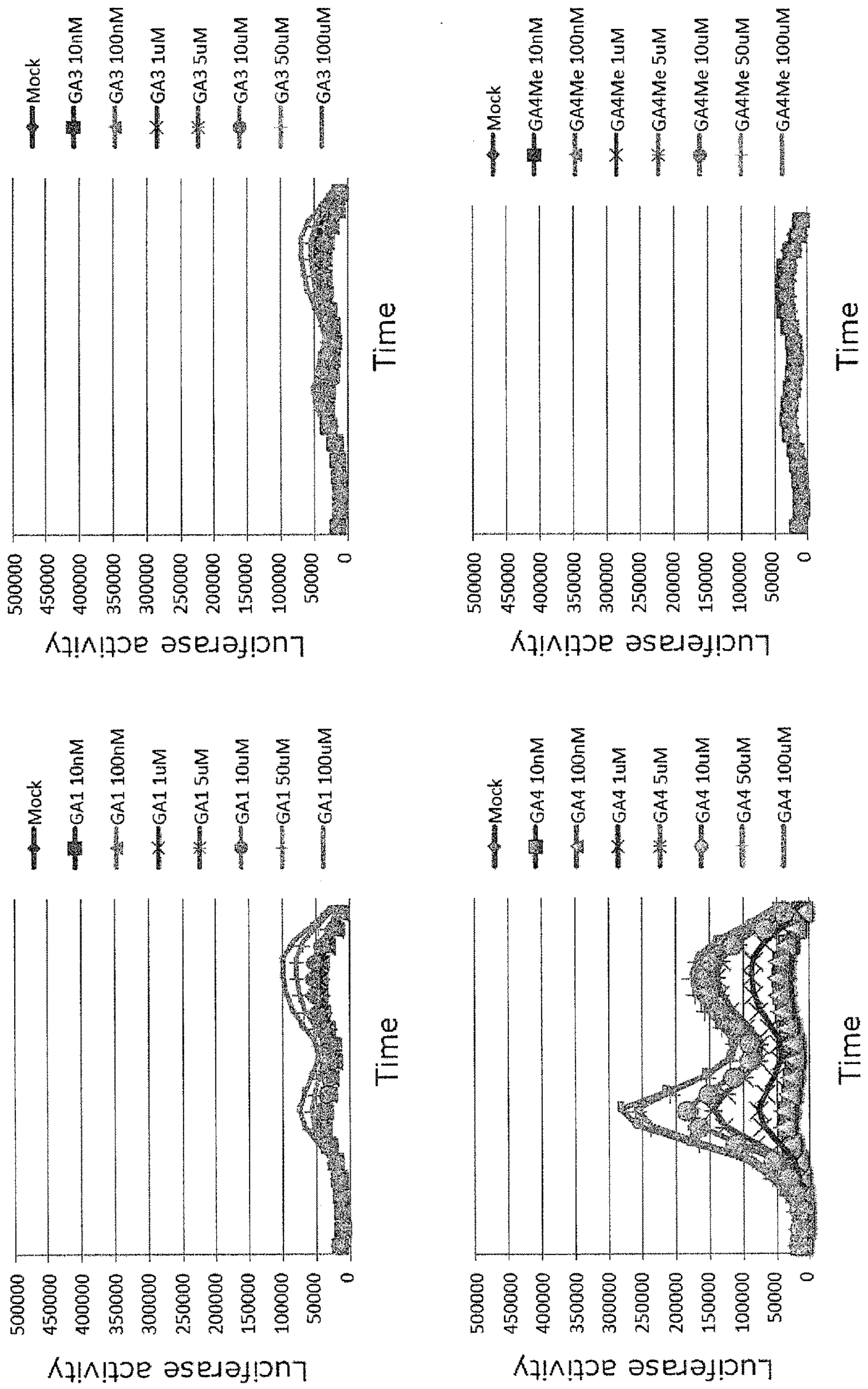
FIGS. 6A-6D: shows results of an inventive assay performed in *Saccharomyces cerevisiae* using an *Arabidopsis thaliana* GID1B based sensor and GID1C based sensor.
Figure 6B:
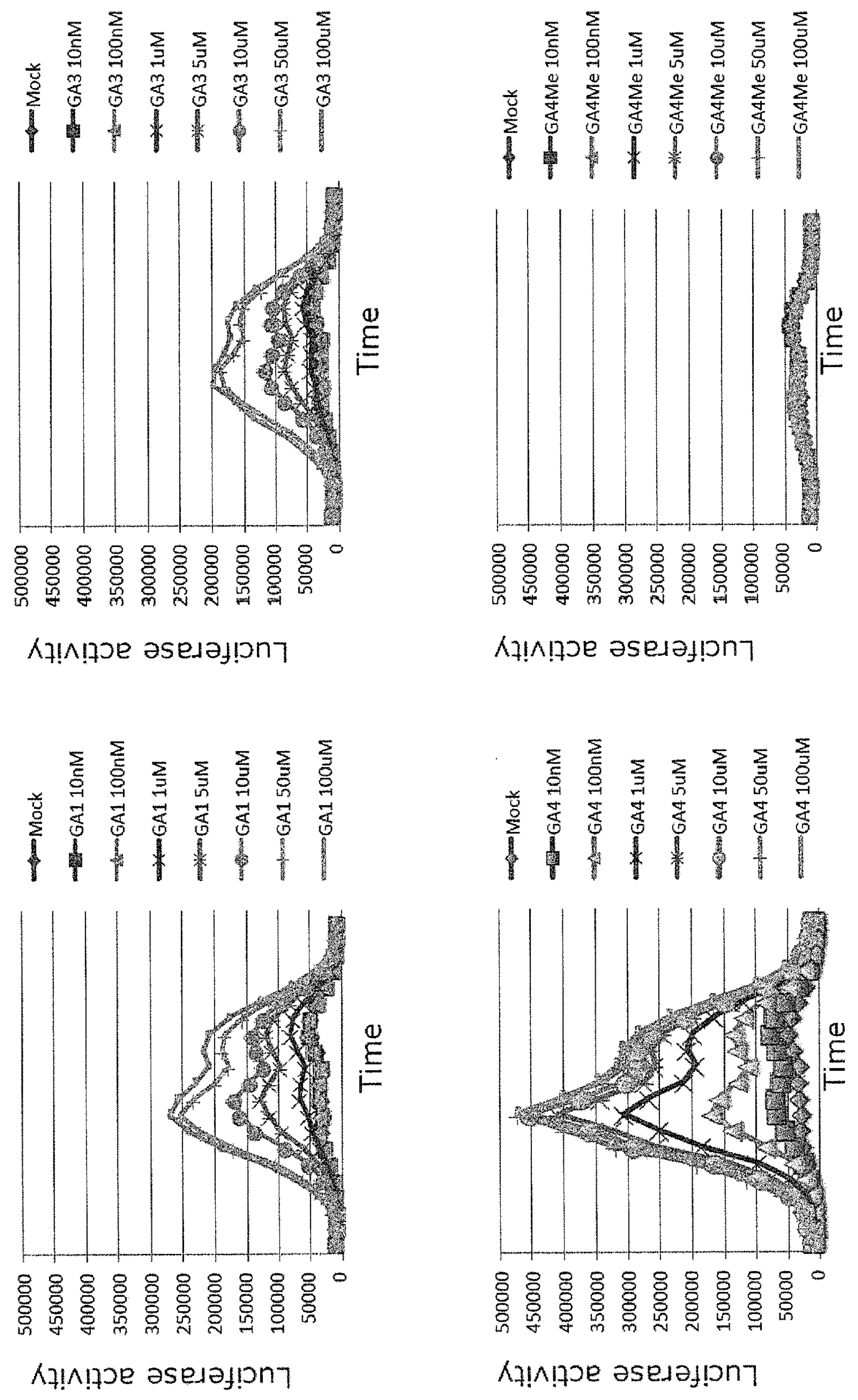
Figure 6C:
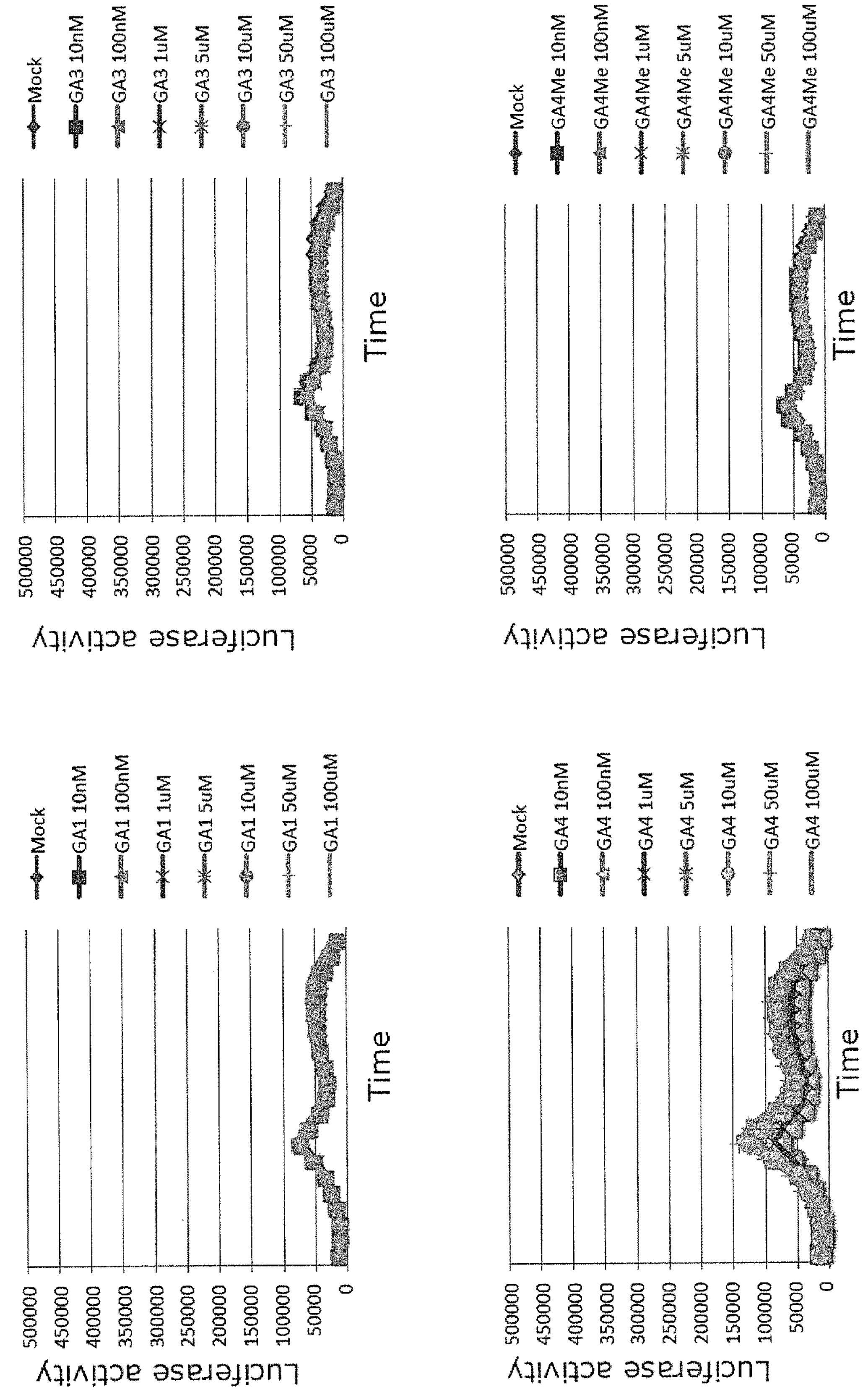
Figure 6D:
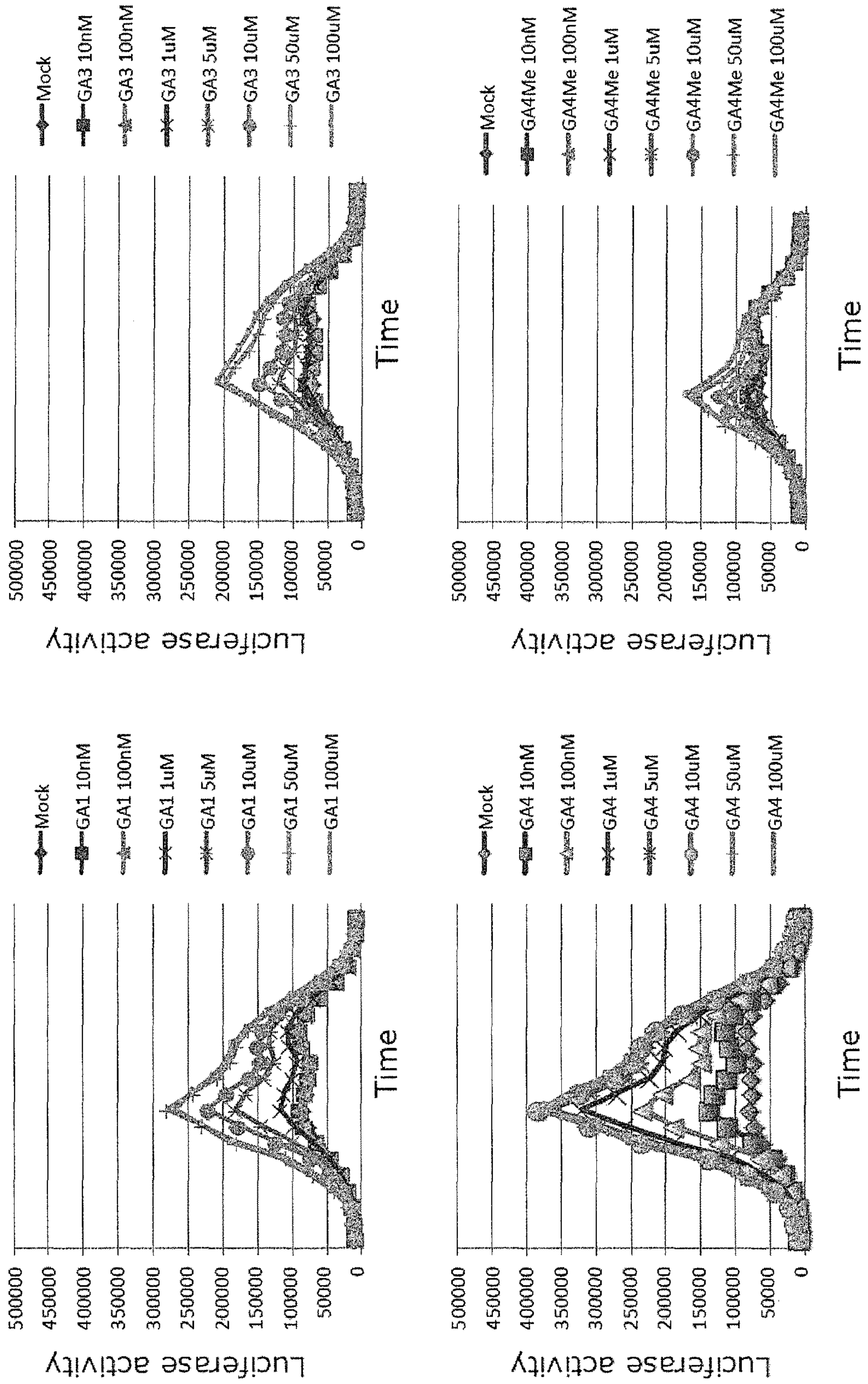

Transformed ga1-3 plants containing the sensor were grown and sprayed either with a negative control solution (mock) or with a 100 μM GA3 solution. The inventors found that upon luciferase substrate application, only the GA-treated plants showed bioluminescence and reported the presence of the hormone (FIG. 4). In this case, the *Arabidopsis thaliana* GID1C based sensor produced a faster and stronger signal than the *Arabidopsis thaliana* GID1B based sensor. To ascertain whether the reporter system according to the invention could quantitatively report the presence of endogenous bioactive GA isoforms, the inventors grew the *Arabidopsis thaliana* Ler-1 wild-type plants containing the *Arabidopsis thaliana* GID1C based sensor along with *Arabidopsis thaliana* GA3ox1-GUS and GA3ox2-GUS reporter lines. The GA sensor was active in a pattern that indicated the presence of active forms of GA in emerging leaves and at the base and vasculature of older leaves. Noticeably, intensity and location of the signal correlated with the activity of both GA biosynthetic enzymes (see FIG. 5). It can be concluded that the *Arabidopsis thaliana* GID1B based sensor is more suitable for in vitro assays and microorganism-based assays, while the *Arabidopsis thaliana* GID1C based sensor is more suitable for in planta experiments.

For luciferase imaging, *Arabidopsis thaliana* plants expressing GA sensors (Ler-1 wild type and ga1-3 mutant) were sprayed 16 hours before imaging with a solution of luciferase substrate supplemented with 0.01% Triton™ X-100. After 16 hours and prior to imaging another spray of that solution was applied. Luminescence was recorded using a CCD camera device (Hamamatsu). GUS (β-glucuronidase) staining in GA3ox1-GUS and GA3ox2-GUS reporter lines was performed as described in Blázquez M A et al., Development 1997, 124: 3835-44.

Example 4: Impact of the Addition of the DELLA Protein GAI

In order to assess the sensitivity and specificity of the inventive sensor peptide to increasing concentrations of different GA isoforms in the presence or absence of the DELLA protein GAI, yeast two-hybrid (Y2H) assays were carried out.

First, the coding sequence of the DELLA protein GAI (At1g14920) was cloned into the yeast plasmid pDEST32 (Invitrogen) yielding the construct IR236. Subsequently, yeast cells were transformed with the plasmids IR206 or IR214 in combination with the empty pDEST32 vector or IR236. Following the same approach than described before in Example 3, we assayed 4 GA isoforms, the same four than in the former assay. The experimental setting was the same than in Example 3 with the difference that the selective media used was deficient in Trp and Leu (YNB, MPBlo, supplemented with CSM $Trp^-Leu^-$, Bio 101) to select for the presence of both plasmids within the yeast cells. Selective media used in Y2H assays was supplemented with Adenine hemisulfate.

As can be seen in FIG. 6, the presence of GAI resulted in higher GA sensitivity of the reporter, which translated into higher levels of luciferase activity both for GID1B and GID1C based sensors. Nevertheless, GAI expression also led to more background, since the presence of non-biological $GA_4$-methylester triggered luciferase signal (FIG. 6D). Thus, the result shows that GID1B is able to report differentially biological forms of GA without the presence of any partner protein. In case of GID1C the presence of an additional binding partner sensitizes the assay.

Example 5: Active Reconstitution of GID1B Based Sensor in Dependence of Overlapping Fragments In order to assess the impact of the presence of overlapping parts of firefly luciferase on the GID1B based sensor (GID1B.5) at the split point, a GID1B based sensor with overlapping firefly luciferase fragments (plasmid IR235) was compared in a Y2H assay to a GID1B based sensor without overlapping firefly luciferase fragments (plasmid IR241).

Four representative colonies were selected and plated onto Nylon membranes as described before. After 3 days at 30° C. the membranes were incubated in selective media containing luciferase substrate for 4 hours in dark at room temperature. Each replicate was subsequently transferred to plates containing selective media supplemented with luciferase substrate. After 4 hours of incubation to minimize signal noise, both membranes were transferred to fresh plates with selective media, luciferase substrate and either mock solution (100% ethanol) or $GA_3$ at a final concentration of 100 μM. Luciferase activity was recorded as indicated before.

As it can be seen in FIG. 7, active reconstitution and thus a lumienscence signal was only reported when the GID1B based sensor included overlapping firefly fragments. Furthermore, luciferase signal is clearly higher when yeasts are incubated in presence of the bioactive $GA_3$.

The invention claimed is:

1. A sensor peptide encompassing, at its N-terminus, a first inactive fragment of a bioluminescent reporter or of a fluorescent reporter followed by a first linker, a gibberellic acid (GA) receptor of the GID1 family, a second linker and, at its C-terminus, a second inactive fragment of the bioluminescent reporter or of the fluorescent reporter and wherein the first and the second inactive fragment of the bioluminescent reporter or of the fluorescent reporter are together suitable to restore functionality of the bioluminescent reporter or of the fluorescent reporter, wherein the sensor peptide has at least 95% sequence identity with SEQ ID No. 2 or with SEQ ID No. 13 over the total length of the aligned sequences.

2. A method of identifying substances that modulate gibberellic acid (GA) action through targeting its receptor or acting as a GA functional analog comprising the following steps:

a) providing a candidate substance to be tested, b) providing a sensor peptide, c) bringing the candidate substance into contact with the sensor peptide, d) providing conditions sufficient to allow the candidate substance to bind to the sensor peptide, e) determining whether the candidate substance binds to the sensor peptide, wherein the sensor peptide encompasses, at its N-terminus, a first inactive fragment of a bioluminescent reporter or of a fluorescent reporter followed by a first linker, a GA receptor of the GID1 family, a second linker and, at its C-terminus, a second inactive fragment of the bioluminescent reporter or of the fluorescent reporter and wherein the first and the second inactive fragment of the bioluminescent reporter or of the fluorescent reporter are together suitable to restore functionality of the bioluminescent reporter or of the fluorescent reporter, and wherein the bioluminescent or fluorescent activity of the sensor peptide is indicative of the binding of the candidate substance to the sensor peptide.

3. The method according to claim 2, wherein the sensor peptide has at least 95% identity to SEQ ID No. 2 or to SEQ ID No. 13 over the total length of the aligned sequences.

4. The method according to claim 2, wherein the method is an in vitro assay.

5. The method according to claim 4, wherein step c) comprises forming a reaction mixture comprising the candidate substance and the sensor peptide.

6. The method according to claim 5, wherein step d) comprises incubating the reaction mixture under conditions sufficient to allow the candidate substance to bind the sensor peptide, in case the candidate substance is able to bind the sensor peptide.

7. The method according to claim 4, wherein step c) comprises producing a cell extract from a host cell able to produce the sensor peptide.

8. The method according to claim 7, wherein step d) comprises incubating the cell extract with the candidate substance under conditions sufficient to allow the candidate substance to bind the sensor peptide, in case the candidate substance is able to bind the sensor peptide.

9. The method according to claim 2, wherein the method is an in vivo assay.

10. The method according to claim 9, wherein step c) comprises transforming or transfecting a host cell or an organism with a nucleic acid coding for the sensor peptide.

11. The method according to claim 10, wherein step c) further comprises transforming or transfecting a host cell or an organism with a nucleic acid coding for the candidate substance or incubating the host cell or an organism with the candidate substance.

12. The method according to claim 2, comprising the following steps:

a) providing a candidate substance to be tested, b) providing a sensor peptide, b') providing a GA or a GA derivative, c) bringing the candidate substance into contact with the sensor peptide and the GA or the GA derivative, d) providing conditions sufficient to allow the candidate substance to bind to the sensor peptide, the GA or to the GA derivative, e) determining whether the candidate substance inhibits the GA or the GA derivative binding to a GA receptor, wherein the sensor is a protein encompassing, at its N-terminus, a sequence that is at least 90% identical with the amino acids 397-550 of the firefly luciferase according to SEQ ID No. 1 followed by a first linker, a GA receptor of the GID1 family, a second linker and, at its C-terminus, a sequence that is at least 90% identical with amino acids 1-416 of the firefly luciferase according to SEQ ID No. 1 and wherein the luciferase activity of the sensor is indicative for the inhibition of the GA or the GA derivative binding by the candidate substance.

13. A nucleic acid molecule that encodes a sensor peptide encompassing, at its N-terminus, a first inactive fragment of a bioluminescent reporter or of a fluorescent reporter followed by a first linker, a GA receptor of the GID1 family, a second linker and, at its C-terminus, a second inactive fragment of the bioluminescent reporter or of the fluorescent reporter and wherein the first and the second inactive fragment of the bioluminescent reporter or of the fluorescent reporter are together suitable to restore functionality of the bioluminescent reporter or of the fluorescent reporter, wherein the sensor peptide has at least 95% sequence identity with SEQ ID No. 2 or SEQ ID No. 13 over the total length of the aligned sequences.

14. Strain AH109 of the species *Saccharomyces cerevisiae* expressing the GID1B based sensor peptide according to SEQ ID No. 2 deposited at the German Collection of Microorganisms and Cell Cultures with deposit number 28095.

* * * * *